(12) United States Patent
Calvert

(10) Patent No.: US 11,708,613 B2
(45) Date of Patent: Jul. 25, 2023

(54) RAPID DETECTION OF ZIKA VIRUS BY REVERSE TRANSCRIPTION LOOP-MEDIATED ISOTHERMAL AMPLIFICATION

(71) Applicant: The U.S.A., as represented by the Secretary, Department of Health and Human Services, Bethesda, MD (US)

(72) Inventor: Amanda E. Calvert, Mead, CO (US)

(73) Assignee: The United States of America, as Represened by the Secretary, Department of Health and Human Services, Bethesda, MD (US)

( * ) Notice: Subject to any disclaimer, the term of this patent is extended or adjusted under 35 U.S.C. 154(b) by 768 days.

(21) Appl. No.: 16/609,994

(22) PCT Filed: Apr. 27, 2018

(86) PCT No.: PCT/US2018/029738
§ 371 (c)(1),
(2) Date: Oct. 31, 2019

(87) PCT Pub. No.: WO2018/204175
PCT Pub. Date: Nov. 8, 2018

(65) Prior Publication Data
US 2020/0063216 A1   Feb. 27, 2020

Related U.S. Application Data

(60) Provisional application No. 62/500,866, filed on May 3, 2017.

(51) Int. Cl.
*C12Q 1/6888* (2018.01)
*C12Q 1/70* (2006.01)
*C12Q 1/6844* (2018.01)

(52) U.S. Cl.
CPC ......... *C12Q 1/6888* (2013.01); *C12Q 1/6844* (2013.01); *C12Q 1/701* (2013.01); *C12Q 2525/301* (2013.01); *C12Q 2531/119* (2013.01); *C12Q 2600/16* (2013.01)

(58) Field of Classification Search
CPC .... C12Q 1/6888; C12Q 1/6844; C12Q 1/701; C12Q 2525/301; C12Q 2531/119; C12Q 2600/16
See application file for complete search history.

(56) References Cited

U.S. PATENT DOCUMENTS

| | | |
|---|---|---|
| 3,827,937 A | 8/1974 | Kato et al. |
| 9,222,126 B2 | 12/2015 | Bearinger et al. |
| 2015/0240293 A1 | 8/2015 | Tanner et al. |
| 2018/0340215 A1* | 11/2018 | Metsky .................. C07H 21/04 |

FOREIGN PATENT DOCUMENTS

| | | |
|---|---|---|
| CN | 106244726 | 12/2016 |
| EP | 0143603 | 6/1985 |
| EP | 0586034 | 3/1994 |
| EP | 0670368 | 2/1995 |
| EP | 2583982 | 4/2013 |
| WO | WO 2016/189490 | 12/2016 |

OTHER PUBLICATIONS

Lanciotti et al. Zika virus strain PRVABC59, complete genome. Gen Bank Accession No. KU501215 (2016). (Year: 2016).*
Lowe et al. A complete program for selection of oligonucleotide primers for polymerase chain reactions. Nucleic Acids Research (1990) 18:1757-1761. (Year: 1990).*
Eiken Chemical Co., Ltd. (2012) A guide to LAMP primer designing (PrimerExplorer V4).*
Bouveng et al., "Polysaccharides Elaborated by *Pullularia pullulans*," *Acta Chem. Scand.*, vol. 16:615-622, 1962.
Calvert et al., "Rapid Colorimetric Detection of Zika Virus from Serum and Urine Specimens by Reverse Transcription Loop-Mediated Isothermal Amplification (RT-LAMP)," *PLoS One*, vol. 12:e0185340, 2017.
Chotiwan et al., "Rapid and Specific Detection of Asian- and African-Lineage Zika Viruses," *Sci. Transl. Med.*, vol. 9:0538, 2017.
EMBL Database Accession No. JS816281, Mar. 5, 2009.
Integrated DNA Technologies, Designing Antisense Oligonucleotides, pp. 1-16, 2005 and 2011.
Lau et al., "Colorimetric Detection of Dengue by Single Tube Reverse-Transcription-Loop-Mediated Isothermal Amplification," *PLoS One*, vol. 10:e0138694, 2015.
Li et al., "Simultaneous Detection and Differentiation of Dengue Virus Serotypes 1-4, Japanese Encephalitis Virus, and West Nile Virus by a Combined Reverse-Transcription Loop-Mediated Isothermal Amplification Assay," *Virol. J.*, vol. 8:360-369, 2011.
Madi et al., "Effect of Exogenous Calcium on Morphological Development and Biopolymer Synthesis in the fungus *Aureobasidium pullulans*," *Enzyme Microb. Technol.*, vol. 21:102-107, 1997.
Parida et al., "Rapid Detection and Differentiation of Dengue Virus Serotypes by a Real-Time Reverse Transcription-Loop Mediated Isothermal Amplification Assay," *J. Clin. Microbiol.*, vol. 43:2895-2903, 2005.
Parida et al., "Development and Evaluation of Reverse Transcription-Loop-Mediated Isothermal Amplification Assay for Rapid and Real-Time Detection of Japanese Encephalitis Virus," *J. Clin. Microbiol.*, vol. 44:4172-4178, 2006.
Parida et al., "Rapid and Real-Time Detection of Chikungunya Virus by Reverse Transcription Loop-Mediated Isothermal Amplification Assay," *J. Clin. Microbiol.*, vol. 45:351-357, 2007.

(Continued)

*Primary Examiner* — David C Thomas
(74) *Attorney, Agent, or Firm* — Klarquist Sparkman, LLP

(57) ABSTRACT

A highly sensitive and specific reverse transcription loop-mediated isothermal amplification (RT-LAMP) assay to detect ZIKV nucleic acid in biological samples is described. The disclosed assay is capable of detecting as few as one RNA copy per μl and can be performed in a clinical or field setting with minimal equipment and technological expertise. Oligonucleotide primers and kits for detecting ZIKV nucleic acid are also described.

20 Claims, 2 Drawing Sheets
Specification includes a Sequence Listing.

(56) References Cited

OTHER PUBLICATIONS

Peyrefitte et al., "Real-Time Reverse Transcription Loop-Mediated Isothermal Amplification for Rapid Detection of Rift Valley Fever Virus," *J. Clin. Microbiol.*, vol. 46:3653-3659, 2008.

Priye et al., "A Smartphone-Based Diagnostic Platform for Rapid Detection of Zika, Chikungunya, and Dengue Viruses," *Sci. Rep.*, vol. 7:1-11, 2017.

Seo et al., "Production of High Molecular Weight Pullulan by *Aureobasidium pullulans* HP-2001 with Soybean Pomace as a Nitrogen Source," *Biosource Tech.*, vol. 95:293-299, 2004.

Song et al., "Instrument-Free Point-of-Care Molecular Detection of Zika Virus," *Anal. Chem.*, vol. 88:7289-7294, 2016.

Suebsing et al., "Reverse Transcription Loop-Mediated Isothermal Amplification (RT-LAMP) Combined with Colorimetric Gold Nanoparticle (AuNP) Probe Assay for Visual Detection of *Penaeus vannamei* Nodavirus (PvNV)," *Lett. Appl. Microbiol.*, vol. 56:428-435, 2013.

Tanner et al., "Visual Detection of Isothermal Nucleic Acid Amplification Using pH-Sensitive Dyes," *BioTechniques*, vol. 58:59-68, 2015.

Tian et al., "Attomolar Zika Virus Oligonucleotide based on Loop-Mediated Isothermal Amplification and AC Susceptome," *Biosens. Bioelectron.*, vol. 86:420-425, 2016.

Teoh et al., "Early Detection of Dengue Virus by Use of Reverse Transcription-Recombinase Polymerase Amplification," *J. Clin. Microbiol.*, vol. 53:830-837, 2015.

Wang et al., "Rapid and Sensitive Detection of Zika Virus by Reverse Transcription Loop-Mediated Isothermal Amplification," *J. Virol. Methods.*, vol. 238:86-93, 2016.

Wheeler et al., "Surveillance for Western Equine Encephalitis, St. Louis Encephalitis, and West Nile Viruses Using Reverse Transcription Loop-Mediated Isothermal Amplification," *PLoS One*, vol. 11:e0147962, 2016.

\* cited by examiner

SEQUENCE LISTING

```
<160> NUMBER OF SEQ ID NOS: 22

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
tggttccacg acattccatt                                                   20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
catttcaagt ggccagagga                                                   20

<210> SEQ ID NO 3
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 3
ggcatgtgcg tccttgaact ctgacaccgg aactccacac t                           41

<210> SEQ ID NO 4
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 4
agaaggagca gttcacacgg ccoctttgca ccatccatct c                           41

<210> SEQ ID NO 5
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 5
accagtgctt ctttgttgtt cc                                                22

<210> SEQ ID NO 6
<211> LENGTH: 19
<212> TYPE: DNA
```

<213> ORGANISM: Artificial Sequence
<220> FEATURE:
<223> OTHER INFORMATION: Synthetic oligonucleotide

<400> SEQUENCE: 6
ccttgctgga gctctggag                                                    19

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
gatcttggat gtggcagagg                                                   20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
tgcttcttcc acttcaggac                                                   20

<210> SEQ ID NO 9
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 9
cgggttcttc atgaccaggg cgttactacg tcgccaccat c                            41

<210> SEQ ID NO 10
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 10
tccgtcttaa gagtggggtg gatgtcacac agcaacgtgt c                            41

<210> SEQ ID NO 11
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 11
cctttcactt cttgaacttt gcg                                               23

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
cgtctttcat atggcggctg                                                   20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
aatgagtgac ctggctaagc                                          20

<210> SEQ ID NO 14
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 14
aaaagacacg aggccaagg                                           19

<210> SEQ ID NO 15
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 15
cagcgccaga tgagctacat cttttttgatg ggtgccacct tc                42

<210> SEQ ID NO 16
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 16
agcggcattc aaagtcagac catttcacgg ggtgtccaat t                  41

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
cctccagtgt tcatttccgc                                          20

<210> SEQ ID NO 18
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 18
gcgttgctgg tatctttcat ctt                                      23

<210> SEQ ID NO 19
<211> LENGTH: 20
<212> TYPE: DNA
<213> ORGANISM: Artificial Sequence
<220> FEATURE:

```
<223> OTHER INFORMATION: Synthetic oligonucleotide

<400> SEQUENCE: 19
ggaactccac actggaacaa                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
aaccacgaca gtttgccttt                                              20

<210> SEQ ID NO 21
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 21
agagttcaag gacgcacatg cca                                          23

<210> SEQ ID NO 22
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 22
taatacgact cactataggg aga                                          23
```

RAPID DETECTION OF ZIKA VIRUS BY REVERSE TRANSCRIPTION LOOP-MEDIATED ISOTHERMAL AMPLIFICATION

CROSS REFERENCE TO RELATED APPLICATIONS

This application is the U.S. National Stage of International Application No. PCT/US2018/029738, filed Apr. 27, 2018, published in English under PCT Article 21(2), which claims the benefit of U.S. Provisional Application No. 62/500,866, filed May 3, 2017, which is herein incorporated by reference in its entirety.

FIELD

This disclosure concerns a rapid and sensitive point-of-care (POC) diagnostic assay for the detection of Zika virus nucleic acid in biological samples.

BACKGROUND

Zika virus (ZIKV) is a mosquito-borne virus from the genus Flavivirus in the family Flaviviridae. Other notable viruses in this genus are dengue 1-4 viruses (DENV1-4), yellow fever virus (YFV), West Nile virus (WNV) and Japanese encephalitis virus (JEV). ZIKV was first isolated in 1947 from the blood of a febrile sentinel rhesus monkey during a yellow fever study in the Zika forest Uganda (Dick et al., *Trans R Soc Trop Med Hyg* 46:509-520, 1952). Until recently, ZIKV was only known to cause a mild febrile illness with very few cases reported since its discovery. In April 2007, ZIKV caused an epidemic of disease in Yap State. Federated States of Micronesia (Lanciotti et al., *Emerg Infect Dis* 14:1232-1239, 2008), after which the virus spread across the South Pacific for the next 8 years before being identified as the causative agent of an outbreak of disease in March 2015 in Bahia, Brazil (Campos et al., *Emerg Infect Dis* 21:1885-1886, 2015; Zanluca et al., *Mem Inst Oswaldo Cru.* 110:569-572, 2015; Petersen et al., *N Engl J Med* 374:1552-1563, 2016). Since this time, ZIKV has been shown to be transmitted sexually, from mother to fetus, and possibly through blood transfusions (Calvet et al., *Lancet Infect Dis* 16:653-660, 2016; Calvet et al., *Curr Opin Infect Dis* 29:459-466, 2016; D'Ortenzio et al., *N Engl J Med* 374:2195-2198, 2016: Foy et al., *Emerg Infect Dis* 17:880-882, 2011; Musso et al., *Euro Surveill* 19, 2014; Venturi et al., *Euro Surveill* 21, 2016). It has also been shown as the causative agent of microcephaly and other congenital brain abnormalities in infants born to mothers infected during pregnancy (Campos et al., *Emerg Infect Dis* 21:1885-1886, 2015; Petersen et al., *N Engi J Med* 374: 1552-1563, 2016: Heukelbach et al., *Lancet* 388:846-847, 2016: Rasmussen et al., *N Engl J Med* 374:1981-1987, 2016), as well as triggering cases of Guillain-Barre syndrome in infected patients (Brasil et al., *Lancer* 387:1482, 2016; Fauci et al., *N Engl J Med* 374:601-604, 2016).

Laboratory diagnosis of ZIKV relies on analysis of urine or serum for the detection of viral RNA within the first 10 days after symptom onset, or the analysis of serum for IgM by ELISA after the acute phase of disease. Due to the cross-reactivity of flaviviruses during secondary infections, a definitive diagnosis based on serology results is not possible (Lanciotti et al., *Emerg Infect Dis* 14:1232-1239, 2008: Petersen et al., *N Engl J Med* 374:1552-1563, 2016). Some data suggests that ZIKV RNA may be detected longer in urine than from serum (Gourinat et al., *Emerg Infect Dis* 21:84-86, 2015; Korhonen et al., *Euro Surveill* 21, 2016; Kutsuna et al., *Euro Surveill* 19, 2014; Roze et al., *Euro Surveill* 21, 2016). Since the only way ZIKV infections can be definitively diagnosed is through the detection of ZIKV RNA during the acute phase of infection, a rapid diagnostic assay that can be performed throughout pregnancy in a clinical setting is vital for prenatal care of women living in areas of possible transmission of the virus.

Loop-mediated isothermal amplification (LAMP) developed by Notomi et al. (*Nucleic Acids Res* 28:E63, 2000) is a technique for the amplification of nucleic acid utilizing 4-6 primers designed to amplify the gene target through creation of stem-loop structures that aid in synthesizing new DNA by the polymerase. Synthesis of DNA occurs rapidly at a constant temperature, unlike PCR which requires specialized equipment for temperature cycling. LAMP is also highly specific, since several primers are used to amplify a specific nucleic acid sequence. Reverse-transcription LAMP (RT-LAMP) assays have previously been developed for the rapid detection of several mosquito-borne viruses in humans and mosquito pools including DENV, WNV, YFV, chikungunya virus (CHIKV), Rift Valley fever virus (RVFV). St. Louis encephalitis virus (SLEV) and Western equine encephalitis virus (Li et al., *Virol J* 8:360, 2011; Parida et al., *Clin Microbiol* 43:2895-2903, 2005; Parida et al., *Clin Microbiol* 45:351-357, 2007; Parida et al., *Clin Microbiol* 44:4172-4178, 2006; Peyrefitte et al., *Clin Microbiol* 46:3653-3659, 2008; Teoh et al., *BMC Infect Dis* 13:387, 2013; Toriniwa and Komiya, *Microbiol Immunol* 50:379-387, 2006; Wheeler et al., *PLoS One* 2016; 11:e0147962).

SUMMARY

Disclosed herein are methods and kits for detection of ZIKV nucleic acid in biological samples. The disclosed methods and kits allow for the rapid, sensitive and specific diagnosis of ZIKV infection in POC settings.

Provided herein is a method for detecting ZIKV nucleic acid in a biological sample. In some embodiments, the method includes subjecting the sample to a reverse transcription loop-mediated isothermal amplification (RT-LAMP) reaction using a set of primers specific for ZIKV nucleic acid to produce a ZIKV nucleic acid amplification product; and detecting the ZIKV nucleic acid amplification product. In particular embodiments, the RT-LAMP reaction includes a pH sensitive indicator dye, such as a dye detectable in visible light.

Also provided herein are kits for detecting ZIKV nucleic acid in a biological sample. In some embodiments, the kit includes a set of primers specific for ZIKV nucleic acid, such as primers that can be used in an RT-LAMP assay for detection of ZIKV nucleic acid. In some examples, the kit further includes one or more of buffer, reverse transcriptase and DNA polymerase.

Further provided herein are oligonucleotide primers for detection of ZIKV nucleic acid. In some embodiments, the primers have a sequence at least 85% identical to any one of SEQ ID NOs: 1-18.

The foregoing and other features and advantages will become more apparent from the following detailed description of several embodiments, which proceeds with reference to the accompanying figures.

SEQUENCE LISTING

Figure 1:
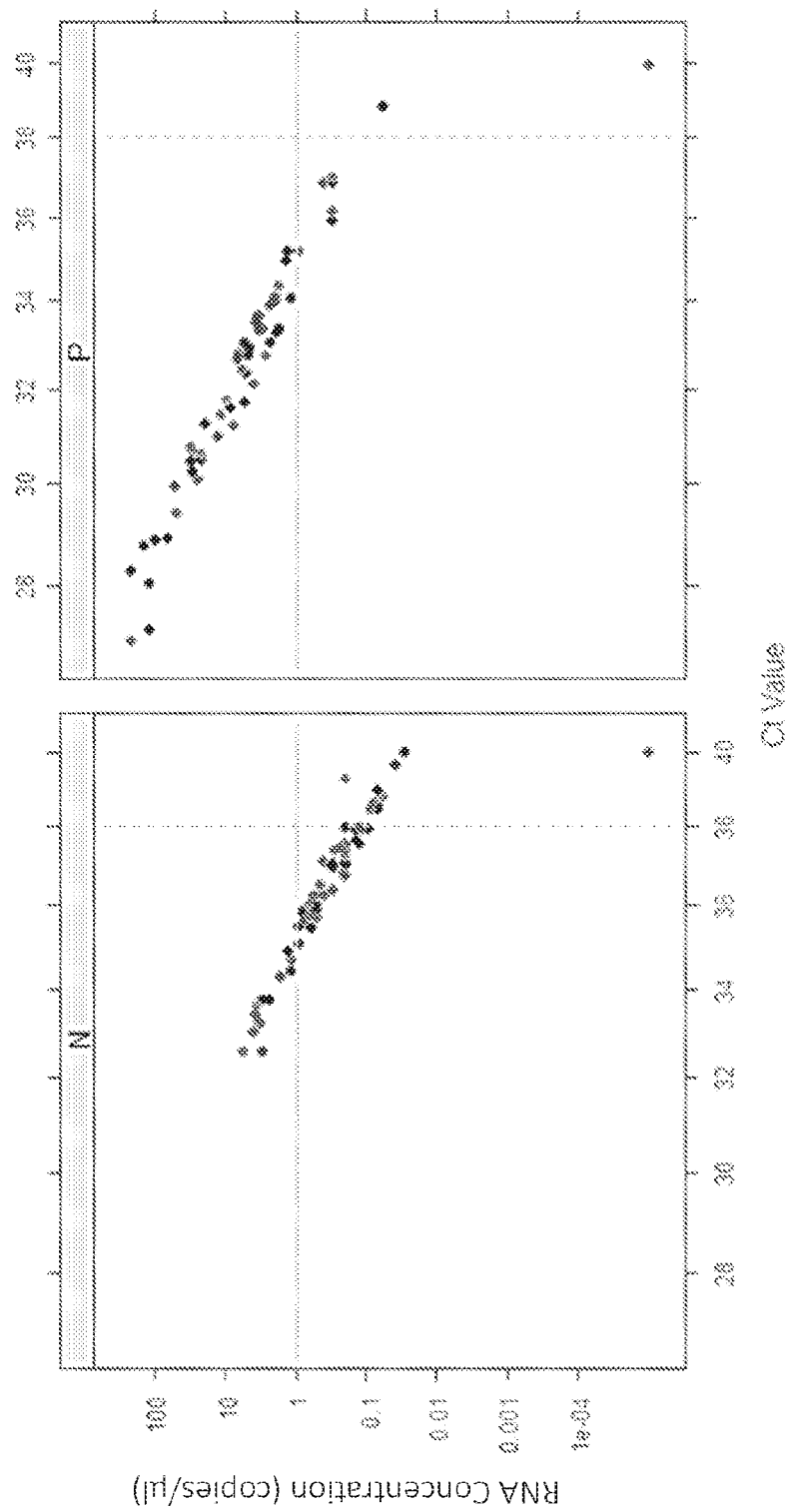
FIG. 1: Evaluation of ZIKV RT-LAMP assay with diagnostic specimens. Negative (N; left) ZIKV RT-LAMP results and positive (P; right) ZIKV RT-LAMP results were separated and plotted out based on Ct value (x-axis) and RNA concentration (y-axis) from the corresponding RT-PCR. Each diamond represents one urine or serum sample. The solid horizontal line represents the 1 RNA copy/pi cutoff value. The dashed vertical line represents the Ct value 38.0. All Ct values >38.0 are considered negative in the RT-PCR.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Sep. 13, 2019, 4.66 KB, which is incorporated by reference herein. In the accompanying sequence listing:

SEQ ID NOs: 1-18 are primer sequences for RT-LAMP.
SEQ ID NOs: 19-21 are primer and probe sequences for qRT-PCR.
SEQ ID NO: 22 is a T7 promoter sequence.

DETAILED DESCRIPTION

I. Abbreviations

CHIKV chikungunya virus
CI confidence interval
CT cycle threshold
DENV dengue virus
JEV Japanese encephalitis virus
LAMP loop-mediated isothermal amplification
LOD limit of detection
MM master mix
NS non-structural
POC point-of-care
RT reverse transcriptase
RT-LAMP reverse transcription loop-mediated isothermal amplification
RVFV Rift Valley fever virus
SLEV St. Louis encephalitis virus
WNV West Nile virus
YFV yellow fever virus
ZIKV Zika virus

II. Terms and Methods

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Amplification: Increasing the number of copies of a nucleic acid molecule, such as a gene or fragment of a gene, for example at least a portion of ZIKV nucleic acid molecule. The products of an amplification reaction are called amplification products. An example of in vitro amplification is the polymerase chain reaction (PCR), in which a sample (such as a biological sample from a subject) is contacted with a pair of oligonucleotide primers, under conditions that allow for hybridization of the primers to a nucleic acid molecule in the sample. The primers are extended under suitable conditions, dissociated from the template, and then re-annealed, extended, and dissociated to amplify the number of copies of the nucleic acid molecule. Other examples of in vitro amplification techniques include real-time PCR, quantitative real-time PCR (qPCR), reverse transcription PCR (RT-PCR), quantitative RT-PCR (qRT-PCR), loop-mediated isothermal amplification (LAMP; see Notomi et al., *Nucl. Acids Res.* 28:e63, 2000); reverse-transcription LAMP (RT-LAMP); strand displacement amplification (see U.S. Pat. No. 5,744,311); transcription-mediated amplification (U.S. Pat. No. 5,399,491) transcription-free isothermal amplification (see U.S. Pat. No. 6,033,881); repair chain reaction amplification (see WO 90/01069); ligase chain reaction amplification (see U.S. Pat. No. 5,686,272); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Animal: Living multi-cellular vertebrate organisms, a category that includes, for example, mammals and birds. The term mammal includes both human and non-human mammals. Similarly, the term "subject" includes both human and veterinary subjects, for example, humans, non-human primates, dogs, cats, horses, and cows.

Biological sample: A sample obtained from a subject (such as a human or veterinary subject). Biological samples, include, for example, fluid, cell and/or tissue samples. In some embodiments herein, the biological sample is a fluid sample. Fluid sample include, but are not limited to, serum, urine, blood, plasma, feces, saliva, cerebral spinal fluid (CSF) and bronchoalveolar lavage (BAL) fluid.

Contacting: Placement in direct physical association; includes both in solid and liquid form. "Contacting" is often used interchangeably with "exposed." For example, contacting can occur in vitro with one or more primers and/or probes and a biological sample (such as a sample including nucleic acids) in solution.

Control: A reference standard, for example a positive control or negative control. A positive control is known to provide a positive test result. A negative control is known to provide a negative test result. However, the reference standard can be a theoretical or computed result, for example a result obtained in a population.

Detectable label: A compound or composition that is conjugated (e.g., covalently linked) directly or indirectly to another molecule (such as a nucleic acid molecule) to facilitate detection of that molecule. Specific non-limiting examples of labels include fluorescent and fluorogenic moieties (e.g., fluorophores), chromogenic moieties, haptens (such as biotin, digoxigenin, and fluorescein), affinity tags, and radioactive isotopes (such as $^{32}P$, $^{33}P$, $^{35}S$, and $^{125}I$). The label can be directly detectable (e.g., optically detectable) or indirectly detectable (for example, via interaction with one or more additional molecules that are in turn detectable).

Methods for labeling nucleic acids, and guidance in the choice of labels useful for various purposes, are discussed, e.g., in Green and Sambrook, *Molecular Cloning: A Laboratory Manual*, Cold Spring Harbor Laboratory Press, Fourth Edition, 2012, and Ausubel et al., *Short Protocols in Molecular Biology, Current Protocols*, Fifth Edition, 2002.

Fluorescent indicator dye: A fluorescent compound that responds to changes in environmental conditions (such as pH or metal ion concentration) by changes in fluorescence properties. In some examples, fluorescence of a fluorescent indicator dye is increased by a change in pH. The fluorescent indicator dye can be detected by any suitable method, including visually (e.g., under ambient or ultraviolet light) or using instrumentation for detection of fluorescence (such as a fluorimeter or real-time PCR system). Exemplary fluorescent indicator dyes include, for example, calcein, hydroxynaphthol blue, Mag-Fura-2 and Magnesium Green (Life Technologies, Grand Island, N.Y.) and Fluo-2 Mg, Fura-2 Mg. Indo-1 Mg, and Asante Magnesium Green (TEF Labs. Austin, Tex.). In some examples, fluorescence from the fluorescent indicator dyes useful in the methods disclosed herein is visibly detectable (for example, by eye, such as a colorimetric reagent), while in other examples, the fluorescence is detectable using an instrument, such as a fluorimeter or real-time PCR platform.

Isolated: An "isolated" or "purified" biological component (such as a nucleic acid, peptide, protein, protein complex, or virus-like particle) has been substantially separated, produced apart from, or purified away from other biological components in the cell of the organism in which the component naturally occurs, that is, other chromosomal and extrachromosomal DNA and RNA, and proteins. Nucleic acids, peptides and proteins that have been "isolated" or "purified" thus include nucleic acids and proteins purified by standard purification methods. The term also embraces nucleic acids, peptides and proteins prepared by recombinant expression in a host cell, as well as chemically synthesized nucleic acids or proteins. The term "isolated" or "purified" does not require absolute purity; rather, it is intended as a relative term. Thus, for example, an isolated biological component is one in which the biological component is more enriched than the biological component is in its natural environment within a cell, or other production vessel. Preferably, a preparation is purified such that the biological component represents at least 50%, such as at least 70%, at least 90%, at least 95%, or greater, of the total biological component content of the preparation.

Isothermal amplification: Nucleic acid amplification that is not dependent on significant changes in temperature (in contrast to PCR, for example). Thus, it is carried out substantially at about the same single temperature. In some examples, isothermal amplification is substantially isothermal, for example, may include small variations in temperature, such as changes in temperature of no more than about 1-2° C. during the amplification reaction. In one example, isothermal amplification is carried out at about 65° C.

Loop-mediated isothermal amplification (LAMP): A method for amplifying nucleic acid. The method is a single-step amplification reaction utilizing a DNA polymerase with strand displacement activity (e.g., Notomi et al., *Nucl. Acids. Res.* 28:E63, 2000; Nagamine et al., *Mol. Cell. Probes* 16:223-229, 2002; Mori et al., *J. Biochem. Biophys. Methods* 59:145-157, 2004). At least four primers, which are specific for eight regions within a target nucleic acid sequence, are typically used for LAMP; however, in some examples, two primers may be used for LAMP. The primers include a forward outer primer (F3), a backward outer primer (B3), a forward inner primer (FIP), and a backward inner primer (BIP). A forward loop primer (Loop F or LF), and/or a backward loop primer (Loop B or LB) can also be included in some embodiments. The amplification reaction produces a stem-loop DNA with inverted repeats of the target nucleic acid sequence. To amplify RNA sequences using LAMP, reverse transcriptase (RT) is added to the reaction. This variation is referred to as RT-LAMP. In contrast to PCR, LAMP and RT-LAMP are carried out at a constant temperature and do not require a thermal cycler.

pH-sensitive indicator dye: A dye that undergoes a color change as pH increases or decreases. In the context of the present disclosure, pH-sensitive indicator dyes can be used to detect nucleic acid amplification products. When a DNA polymerase incorporates a deoxynucleoside triphosphate into a nascent DNA, the released by-products include a pyrophosphate moiety and a hydrogen ion. Thus, as nucleic acid amplification products increase in a reaction, the pH of the solution decreases, resulting in a color change of the pH-sensitive dye (see Tanner et al. *BioTechniques* 58:59-68, 2015). Exemplary pH-sensitive indicator dyes include, but are not limited to, phenol red, cresol red, neutral red, m-cresol purple, bromocresol purple, naphtholphthalein, thymol blue and naphtolphthalein.

Primer: Primers are short nucleic acids, generally DNA oligonucleotides 10 nucleotides or more in length (such as 10-60, 15-50, 20-40, 20-50, 25-50, or 30-60 nucleotides in length). Primers may be annealed to a complementary target DNA strand by nucleic acid hybridization to form a hybrid between the primer and the target DNA strand, and then extended along the target DNA strand by a DNA polymerase enzyme. Primer pairs or sets of primers (such as 2, 3, 4, 5, 6, or more primers) can be used for amplification of a target nucleic acid, e.g., by PCR, LAMP. RT-LAMP, or other nucleic acid amplification methods known in the art.

Probe: A probe typically comprises an isolated nucleic acid (for example, at least 10 or more nucleotides in length, such as 10-60, 15-50, 20-40, 20-50, 25-50, or 30-60 nucleotides in length) with an attached detectable label or reporter molecule. Exemplary labels include radioactive isotopes, ligands, haptens, chemiluminescent agents, fluorescent molecules (e.g., fluorophores), and enzymes. Methods for labeling oligonucleotides and guidance in the choice of labels appropriate for various purposes are discussed, e.g., in Green and Sambrook, *Molecular Cloning: A Laboratory Manual*, Cold Spring Harbor Laboratory Press, Fourth Edition, 2012, and Ausubel et al., *Short Protocols in Molecular Biology*, Current Protocols, Fifth Edition, 2002.

Recombinant nucleic add: A nucleic acid molecule that is not naturally occurring or has a sequence that is made by an artificial combination of two otherwise separated segments of nucleotide sequence. This artificial combination is accomplished by chemical synthesis or by the artificial manipulation of isolated segments of nucleic acids, e.g., by genetic engineering techniques such as those described in Sambrook and Russell, in *Molecular Cloning: A Laboratory Manual*, $3^{rd}$ Ed., Cold Spring Harbor Laboratory Press (2001). The term "recombinant" includes nucleic acids that have been altered solely by addition, substitution, or deletion of a portion of a natural nucleic acid molecule. A recombinant nucleic acid also includes a heterologous nucleic acid that is inserted in a vector. A "heterologous nucleic acid" refers to a nucleic acid that originates from a different genetic source or species.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls, in the Biosciences* 8, 155-65, 1992: and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Serum: The fluid portion of the blood that separates out from clotted blood. Serum contains many proteins, including antibodies, but does not contain clotting factors.

Subject: Living multi-cellular vertebrate organisms, a category that includes both human and non-human animals, such as non-human mammals (such as mice, rats, rabbits, sheep, horses, cows, and non-human primates).

Zika virus (ZIKV): A member of the virus family Flaviviridae and the genus Flavivirus. Other members of this genus include dengue virus, yellow fever virus, Japanese encephalitis virus. West Nile virus and Spondweni virus. ZIKV is spread by the daytime-active mosquitoes *Aedes aegypti* and *A. albopictus*. This virus was first isolated from a Rhesus macaque from the Zika Forest of Uganda in 1947. Since the 1950s, ZIKV has been known to occur within a narrow equatorial belt from Africa to Asia. The virus spread eastward across the Pacific Ocean in 2013-2014, resulting in ZIKV outbreaks in Oceania to French Polynesia, New Caledonia, the Cook Islands, and Faster Island. In 2015, 71 KV spread to Mexico, Central America, the Caribbean and South America, where ZIKV has reached pandemic levels. Infection by ZIKV generally causes either no symptoms or mild symptoms, including mild headache, maculopapular rash, fever, malaise, conjunctivitis and joint pain. ZIKV causes symptoms in about 20% of infected individuals, and no deaths from the virus have yet been reported. However, ZIKV infection has been linked to the birth of microcephalic infants following maternal infection, as well an increase in cases of GBS. Reports have also indicated that ZIKV has the potential for human blood-borne and sexual transmission. ZIKV has also been found in human saliva and breastmilk.

Unless otherwise explained, all technical and scientific terms used herein have the same meaning as commonly understood by one of ordinary skill in the art to which this disclosure belongs. The singular terms "a." "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Introduction

Zika virus (ZIKV) has emerged as a major global public health concern due to its link as the causative agent of human birth defects. Its rapid expansion into the Western Hemisphere as well as the discovery of new modes of transmission of the virus, including sexual transmission, from mother to fetus, and possibly through blood transfusions, has only increased the need for a rapid and expansive public health response to this unprecedented epidemic. A non-invasive and rapid ZIKV diagnostic assay that can be performed in a clinical setting throughout pregnancy is vital for prenatal care of women living in areas of the world where exposure to the virus is possible. To meet this need, disclosed herein is the development of a highly sensitive and specific reverse transcription loop-mediated isothermal amplification (RT-LAMP) assay to detect ZIKV RNA in biological samples, including urine and serum samples. As little as one RNA copy per µl were detected by RT-LAMP, and the assay was shown to be highly specific for ZIKV RNA when tested against a panel of urine samples spiked with arboviruses that may circulate in the same geographic regions as ZIKV. The ZIKV assay described herein offers a fast, reliable, sensitive and specific assay for the detection of ZIKV from biological samples that can be performed in a clinical or field setting with minimal equipment and technological expertise.

IV. RT-LAMP Assay for Detection of ZIKV RNA

Disclosed herein is a method for the detection of ZIKV nucleic acid in biological samples, such as biological fluid samples, using reverse transcription loop-mediated isothermal amplification (RT-LAMP). The disclosed ZIKV detection assay provides a rapid, sensitive and specific means for diagnosing ZIKV infection in susceptible subjects.

Provided herein is a method for detecting ZIKV RNA in a biological sample by subjecting the sample to an RT-LAMP reaction using a set of primers specific for ZIKV nucleic acid to produce a ZIKV nucleic acid amplification product; and detecting the ZIKV nucleic acid amplification product. In some embodiments, the set of primers includes (a) six primers each respectively having a sequence at least 90%, at least 95%, at least 96%, at least 97%, at least 98% or at least 99% identical to TGGTTCCACGACATTCCATT (F3 1-1; SEQ ID NO: 1); CATTTCAAGTGGCCAGAGGA (B3 1-1; SEQ ID NO: 2); GGCATGTGCGTCCTTGAACTCTGACACCGGAACTCCACACT (FIP 1-1; SEQ ID NO: 3); AGAAGGAGCAGTTCACACGGCCCCTTTGCACCATCCATCTC (BIP 1-1; SEQ ID NO: 4); ACCAGTGCTTCTTGTGTTCC (LF 1-1; SEQ ID NO: 5); and CCTTGCTGGAGCTCTGGAG (LB 1-1; SEQ ID NO: 6); (b) six primers each respectively having a sequence at least 90%, at least 95%, at least 96%, at least 97%, at least 98% or at least 99% identical to GATCTTGGATGTGGCAGAGG (F3 5-5; SEQ ID NO: 7); TGCTTCTTCCACTCAGGAC (B3 5-5; SEQ ID NO: 8) CGGCTTCTCATGACCACiGCGTACTACGTCGCCACCATC (FIP 5-5; SEQ ID NO: 9); TCCGTCTTAAGAGTTGGGGTGGATGTCACACAGCAACGTGTC (BIP 5-5; SEQ ID NO: 10); CCTTTCACTTCTTGAACTTTGCG (LF 5-5; SEQ ID NO: 11); and CGTCTTTCATATGGCGGCTG (LB 5-5; SEQ ID NO: 12); or (c) six primers each respectively having a sequence at least 90%, at least 95%, at least 96%, at least 97%, at least 98% or at least 99% identical to AATGAGTGACCTGGCTAAGC (F3 2-5; SEQ ID NO: 13); AAAAGACACGAGGCCAAGG (B3 2-5; SEQ ID NO: 14); CAGCGCCAGATGAGCTACATCTTTGATGGGTGCCACCTC (FIP 2-5; SEQ ID NO: 15); AGCGGCATTCAAAGTCAGACCATTCACGGGGTGTCCAATT (BIP 2-5; SEQ ID NO: 16); CCTCCATGTTGCATTTCCGC (LF 2-5; SEQ ID NO: 17); and GCGTTGCTGGTATCTTCATCT (LB 2-5; SEQ ID NO: 18).

In some examples, the set of primers includes six primers each respectively having a sequence at least 90%, at least 95%, at least 96%, at least 97%, at least 98% or at least 99% identical to TGGTTCCACGACATTCCATT (F3 1-1; SEQ ID NO: 1); CATTTCAAGTGGCCAGAGGA (B3 1-1; SEQ ID NO: 2); GGCATGTGCGTCCTGAACTCTGACACCGGAACTCCACACT (FIP 1-1; SEQ ID NO: 3); AGAAGGAGCAGTTCACACGGCCCCTTGCACCATCCATCTC (BIP 1-1; SEQ ID NO: 4); ACCAGTGCTTCTTTGTGTTCC (LF 1-1; SEQ ID NO: 5); and CCTTGCTGGAGCTCTGGAG (LB 1-1; SEQ ID NO: 6); and six additional primers each respectively having a sequence at least 90%, at least 95%, at least 96%, at least 97%, at least 98% or at least 99% identical to GATCTTGGATGTGGCAGAGG (F3 5-5; SEQ ID NO: 7); TGCTTCTTCCACTTCAGGAC (B3 5-5; SEQ ID NO: 8); CGGGTTCTTCATGACCAGGGCGTTACTACGTCGCCACCATC (FIP 5-5; SEQ ID NO: 9); TCCGTCTTAAGAGTGGGGTGGATGTCACACAGCAACGTGTC (BIP 5-5; SEQ ID NO: 10); CCTTCACTTCTTGAACTGCG (LF 5-5; SEQ ID NO: 11); and CGTCRTFCATATGCCCTG (LB 5-5; SEQ ID NO: 12).

In other examples, the set of primers includes six primers each respectively having a sequence at least 90%, at least 95%, at least 96%, at least 97%, at least 98% or at least 99% identical to TGGTTCCACGACATTCCATT (F3 1-1; SEQ ID NO: 1); CATTTCAAGTGGCCAGAGGA (B3 1-1; SEQ ID NO: 2); GGCATGTGCGTCCTTGAACTCTGACACCGGAACTCCAC T (FIP 1-1; SEQ ID NO: 3); AGAAGGAGCAGTTCACACGGCCCCTTTGCACCATCCATCTC (BIP 1-1; SEQ ID NO: 4); ACCAGTGCTTCTTGTTGTTCC (LF 1-1; SEQ ID NO: 5); and CCTTGCTGGAGCTCTGGAG (LB 1-1; SEQ ID NO: 6); and six additional primers each respectively having a sequence at least 90%, at least 95%, at least 96%, at least 97%, at least 98% or at least 99% identical to AATGAGTGACCTGGCTAAGC (F3 2-5; SEQ ID NO: 13); AAAAGACACGAGGCCCAAGG (B3 2-5; SEQ ID NO: 14); CAGCGCCAGATGAGCTACATGTFTGATGGGTGCCACCTTC (FIP 2-5; SEQ ID NO: 15); AGCGGCATTCAAAGTCAGACCATTCACGGGGTGTCCAATT (BIP 2-5; SEQ ID NO: 16); CCTCCAGTGTTCATTCCGC (LF 2-5; SEQ ID NO: 17); and GCGTTCGCTCGOTATCTTCATCTT (LB 2-5; SEQ ID NO: 18).

In other examples, the set of primers includes six primers each respectively having a sequence at least 90%, at least 95%, at least 96%, at least 97%, at least 98% or at least 99% identical to GATCTTGGATGTGGCAGAGG (F3 5-5; SEQ ID NO: 7); TGCTTCTTCCACTTCAGGAC (B3 5-5; SEQ ID NO: 8); CGGGTTCTTCATGACCAGGGCGTTATACGTCGCCACCATC (FIP 5-5; SEQ ID NO: 9); TCCGTGTAAGAGTGGOGTGGATGTCACACAGCAACGTGTC (BIP 5-5; SEQ ID NO: 10); CCTGTCACTTCTTGAACTTGCG (LF 5-5; SEQ ID NO: 11); and CGTCTTTCATATGGCGGCTG (LB 5-5; SEQ ID NO: 12); and six additional primers each respectively having a sequence at least 90%, at least 95%, at least 96%, at least 97%, at least 98% or at least 99% identical to AATGAGTGACCTOOCTAAGC (F3 2-5; SEQ ID NO: 13); AAAAGACACGAGGCCAAGG (B3 2-5; SEQ ID NO: 14); CAGCGCCAGATGAGCTACATCTTTTGATGGGTGCCACCTTC (FIP 2-5; SEQ ID NO: 15); AGCGGCATTCAAAGTCAGACCATTCACGGGGTGTCCAAT (BIP 2-5; SEQ ID NO: 16); CCTCCAGTGTCATTCCGC (LF 2-5; SEQ ID NO: 17); and GCGTTGCTGGTATCTTCATCATCT (LB 2-5; SEQ ID NO: 18).

In yet other examples, the set of primers includes six primers each respectively having a sequence at least 90%, at least 95%, at least 96%, at least 97%, at least 98% or at least 99% identical to TGGTTCCACGACATTCCAT (F3 1-1; SEQ ID NO: 1); CATTCAAGTGGCCAGAGGA (B3 1-1; SEQ ID NO: 2); GGCATGTGCGTCCTGAACTCTGACACCCOiAACTCCACACT (FIP 1-1; SEQ ID NO: 3); AGAAGGAGCAGTTCACACGGCCCCTTGCACCACCATCATCTC (BIP 1-1; SEQ ID NO: 4); ACCAGTGCTTCTTTGTTGTTCC (LF 1-1; SEQ ID NO: 5); and CCTTGCTGGAGCTCTGGAG (LB 1-1; SEQ ID NO: 6); six additional primers each respectively having a sequence at least 90%, at least 95%, at least 96%, at least 97%, at least 98% or at least 99% identical to GATCTTGGATGTGGCAGAGG (F3 5-5; SEQ ID NO: 7); TGCTTCTTCCACTTCAGGAC (B3 5-5; SEQ ID NO: 8); CGGGTTCTTCATGACCAGGGCGTTAC TACGTCGCCACCATC (FIP 5-5; SEQ ID NO: 9); TCCGTCTTAAGAGTGGGGTGGATGTCACACAGCAACGTGTC (BIP 5-5; SEQ ID NO: 10); CCTTTCACTTCTTGAACTGCG (LF 5-5; SEQ ID NO: 11); and CGTCTTCATATGGCGGCTG (LB 5-5; SEQ ID NO: 12); and six additional primers each respectively having a sequence at least 90%, at least 95%, at least 96%, at least 97%, at least 98% or at least 99% identical to AATGAGTGACCTGCTCTAAGC (F3 2-5; SEQ ID NO: 13); AAAAGACACGAGGCCAAGG (B3 2-5; SEQ ID NO: 14); CAGCGCCAGATGAGCTACATCTTTTGATGGGTGCCACCTTC (FIP 2-5; SEQ ID NO: 15); AGCGGCATTCAAAGTCAGACCATTCACGGGGTGTCCAATT (BIP 2-5; SEQ ID NO: 16); CCTCCAGTGTTCATTTCCGC (LF 2-5; SEQ ID NO: 17); and GCGTTGCTGGTATCTTTCATCTT (LB 2-5; SEQ ID NO: 18).

In specific examples, the set of primers includes (a) six primers each respectively having a sequence comprising or consisting of TGGTTCCACGACATTCCATT (F3 1-1; SEQ ID NO: 1); CATTCAAGTGGCCAGAGGA (B3 1-1; SEQ ID NO: 2); GGCATGTGCGTCCTGAACTCTGACACCCGOAACTCCACACT (FTP 1-1; SEQ ID NO: 3); AGAAGGAGCAGTCACACGGCCCCTGCACCATCCATCTC (BIP 1-1; SEQ ID NO: 4); ACCAGTGCTCTTGTGTTCC (LF 1-1; SEQ ID NO: 5); and CCTTGCTGGAGCTCTGGAG (LB 1-1; SEQ ID NO: 6); (b) six primers each respectively having a sequence comprising or consisting of GATCTGGATGTGGCAGAGG (F3 5-5; SEQ ID NO: 7); TGCTTCTTCCACTTCAGGAC (B3 5-5; SEQ ID NO: 8); CGGGTTCTTCATGACCAGGGCGTTACTACGTCGCCACCATC (FIP 5-5; SEQ ID NO: 9); TCCGTCTTAAGAGTGGGGTGGATGTCACACAGCAACGTGTC (BIP 5-5; SEQ ID NO: 10); CCTTCACTCTTGAACTTGCG (LF 5-5; SEQ ID NO: 11); and CGTCTTCATATGGCGGCTG (LB 5-5; SEQ ID NO: 12); or (c) six primers each respectively having a sequence comprising or consisting of AATGAGTGACCTGGCTAAGC (F3 2-5; SEQ ID NO: 13); AAAAGACACGAGGCCAAGG (B3 2-5; SEQ ID NO: 14); CAGCGCCAGATGAGCTACATCTTTTGATGGGTGCCACCTTC (FIP 2-5; SEQ ID NO: 15); AGCGGCATTCAAAGTCAGACCATTCACGGGGTGTCCAAT (BIP 2-5; SEQ ID NO: 16); CCTCCAGTGTTCATTCCGC (LF 2-5; SEQ ID NO: 17); and GCGTTGTGGTATCTTTCATCT (LB 2-5; SEQ ID NO: 18).

In other specific examples, the set of primers includes six primers each respectively having a sequence comprising or consisting of TGGTTCCACGACATTCCATT (F3 1-1; SEQ ID NO: 1); CATTTCAAGTGGCCAGAGGA (B3 1-1; SEQ ID NO: 2); GGCATGTGCGTCCTGAACTCTGACACCGGAACTCCACT (FIP 1-1; SEQ ID NO: 3); AGAAGGAGCAGTCACACGGCCCCTTTGCACCATCCATCTC (BIP 1-1; SEQ ID NO: 4); ACCAGTGCTTCTTGTTGTTCC (LF 1-1; SEQ ID NO: 5); and CCTTGCTGGAGCTCTGGAG (LB 1-1; SEQ ID NO: 6); and six additional primers each respectively having a sequence comprising or consisting of GATCTTGGATGTGGCAGAGG (F3 5-5; SEQ ID NO: 7); TCCTCTTCCACTTCAGGAC (B3 5-5; SEQ ID NO: 8); CGGGTCTCATGACCAGGGCGTTACTACGTCGCCACCATC (FIP 5-5; SEQ ID NO: 9); TCCGTCTTAAGAGTGGGGTGGATGTCACACAGCAACGTGTC (BIP 5-5; SEQ ID NO: 10); CCTTTCACTTCTTGAACTTGCG (LF 5-5; SEQ ID NO: 11); and CGTCTTCATATGGCGGCTG (LB 5-5; SEQ ID NO: 12).

In other specific examples, the set of primers includes six primers each respectively having a sequence comprising or consisting of TGGTTCCACGACATTCCAT (F3 1-1; SEQ ID NO: 1); CATTTCAAGTGGCCAGAGGA (B3 1-1; SEQ ID NO: 2); GGCATGTGCGTCCTGAACTCTGACACCGGAACTCCACTAC (FIP 1-1; SEQ ID NO: 3); AGAAGGAGCAGTTCACACGGCCCCTTTGCACCATCCATCTC (BIP 1-1; SEQ ID NO: 4); ACCAGTGCTTCTGGTTGTTCC (LF 1-1; SEQ ID NO: 5); and CCTTCCTGGAGCTCTGGAG (LB 1-1; SEQ ID NO: 6); and six additional primers each respectively having a sequence comprising or consisting of AATGAGTGACCTGGCTAAGC (F3 2-5; SEQ ID NO: 13); AAAAGACACGAGGCCAAGG (B3 2-5; SEQ ID NO: 14); CAGCGCCAGATGAGCTACATCTTTTGATGGGTGCCACCTTC (FIP 2-5; SEQ ID NO: 15); AGCGGCATTCAAAGTCAGACCATTFTCACGGGGTGTCCAATT (BIP 2-5; SEQ ID NO: 16); CCTCCAGTGTTCATTTCCGC (LF 2-5; SEQ ID NO: 17); and GCGTTGCTGGTATCTTTCATCTT (LB 2-5; SEQ ID NO: 18).

In other specific examples, the set of primers includes six primers each respectively having a sequence comprising or consisting of GATCTTGGATGTGGCAGAGG (F3 5-5; SEQ ID NO: 7); TGCTTCTTCCACTTCAGGAC (B3 5-5; SEQ ID NO: 8): CGGGTTCTTCATGACCAGGGCGTTACTACGTCGCCACCATC (FIP 5-5; SEQ ID NO: 9): TCCGTCTTAAGAGTGCGGGTGGATGTCACACAGCAACGTGTC (BIP 5-5; SEQ ID NO: 10); CCTTCACTTCTTGAACTTGCG (LF 5-5; SEQ ID NO: 11); and CGTCTTCATATGCCGOCTG (LB 5-5; SEQ ID NO: 12); and six additional primers each respectively having a sequence comprising or consisting of AATGAGTGACCTGGCTAAGC (F3 2-5; SEQ ID NO: 13); AAAAGACACGAGGCCAAGG (B3 2-5; SEQ ID NO: 14); CAGCGCCAGATGAGCTACATCTTTGATGGGTGCCACCTTC (FIP 2-5; SEQ ID NO: 15); AGCGGCATTCAAAGTCAGACCATTCACGGGGTGTCCAATI (BIP 2-5; SEQ ID NO: 16); CCTCCAGTGTTCATTTCCGC (LF 2-5; SEQ ID NO: 17); and GCGTTGCTGGTATCTCATCTT (LB 2-5; SEQ ID NO: 18).

In one specific non-limiting example, the set of primers includes six primers each respectively having a sequence comprising or consisting of TGGTTCCACGACATTCCATT (F3 1-1; SEQ ID NO: 1); CATTTCAAGTGGCCAGAGGA (B3 1-1; SEQ ID NO: 2); GGCATGTGCGTCCTGAACTCTGACACCGAACTCCACACT (FIP 1-1; SEQ ID NO: 3); AGAAGGAGCAGTCACACGGCCCCFTGCACCATCCATCIC (BIP 1-1; SEQ ID NO: 4): ACCAGTGCTTCTTTGTGTCC (LF 1-1; SEQ ID NO: 5); and CCTTGCTGGAGCTCTGGAG (LB 1-1; SEQ ID NO: 6); six additional primers each respectively having a sequence comprising or consisting of GATCTTGGATGTGGCAGAGG (F3 5-5; SEQ ID NO: 7); TGCTCTTCCACTTCAGGAC (B3 5-5; SEQ ID NO: 8); CGGGCTTCATGACCAGGGCGGTTACTACGTCGCCACCATC (FIP 5-5; SEQ ID NO: 9); TCCGTCTTAAGAGTGGGGTGGATGTCACACAGCAACGTGTC (BIP 5-5; SEQ ID NO: 10); CCTTTCACTTCTTGAACTTTGCG (LF 5-5; SEQ ID NO: 11); and CGTCTTTCATATGGCGGCTG (LB 5-5; SEQ ID NO: 12); and six additional primers each respectively having a sequence comprising or consisting of AATGAGTGACCTGGCTAAGC (F3 2-5; SEQ ID NO: 13); AAAAGACACGAGGCCAAGG (B3 2-5; SEQ ID NO: 14): CAGCGCCAGATGAGCTACATCTTTTGATGGGTGCCACCTTC (FIP 2-5; SEQ ID NO: 15); AGCGGCATTCAAAGTCAGACCATTCACGGGGTGTCCAAT (BIP 2-5; SEQ ID NO: 16); CCTCCAGTGTTCATTTCCGC (LF 2-5; SEQ ID NO: 17); and GCGTTGCTGGTATCTTTCATCTT (LB 2-5; SEQ ID NO: 18).

In some embodiments, the RT-LAMP reaction is performed at about 60° C. to about 68° C., such as about 63° C. to about 67° C., or about 64° C. to about 66° C. In some examples, the RT-LAMP reaction is performed at about 60° C., about 61° C. about 62° C. about 63° C., about 64° C., about 65° C., about 66° C., about 67° C. or about 68° C. In specific examples, the RT-LAMP reaction is performed at 65° C.

In some embodiments, the RT-LAMP reaction is allowed to proceed for about 15 to about 45 minutes, such as about 20 minutes to about 40 minutes, or about 25 minutes to about 35 minutes. In some examples, the RT-LAMP reaction is allowed to proceed for about 30 minutes. In some examples, the RT-LAMP reaction is allowed to proceed for no more than 20 minutes, no more than 25 minutes, no more than 30 minutes, no more than 35 minutes, no more than 40 minutes or no more than 45 minutes.

In some embodiments, the RT-LAMP reaction includes a pH-sensitive indicator dye. In some examples, the pH-sensitive indicator dye is a colored dye detectable in visible light. In particular examples, the colored dye comprises cresol red, phenol red, m-cresol purple, bromocresol purple, neutral red, naphtholphthalein, thymol blue or naphtolphthalein. In other examples, the pH-sensitive indicator dye is a fluorescent indicator dye. In particular examples, the fluorescent dye comprises 2',7-bis-(2-carboxyethyl)-5(6)-carboxyfluorescein, 5(6)-carboxy-2',7'-dichlorofluorescein, 5(6)-carboxyfluorescein, 3,6-diacetoxyphthalonitrile, 6,8-dihydroxy-1,3-pyrenedisulfonic acid, or 5-(and-6)-carboxyl seminaphthorhodafluor.

In some embodiments, detecting the ZIKV nucleic acid amplification product comprises detecting a visible color change. In other embodiments, detecting the ZIKV nucleic acid amplification product comprises detecting fluorescence. In other embodiments, detecting the ZIKV nucleic acid amplification product comprises measuring turbidity.

In some embodiments, the biological sample is a biological fluid sample. In some examples, the biological fluid sample comprises serum, urine, blood, plasma, feces, saliva and/or CSF. In specific examples, the biological sample comprises serum or urine.

The DNA polymerase used in the RT-LAMP reaction can be any enzyme appropriate for the assay, which can be selected by one of skill in the art. In some embodiments, the RT-LAMP reaction includes a DNA polymerase with high strand displacement activity. In some examples, the DNA polymerase is a DNA polymerase long fragment (LF) of a thermophilic bacteria such as *Bacillus stearothermophilus* (Bst). *Bacillus Smithii* (Bsm), *Geobacillus* sp. M (GspM) or *Thermodesulfatator indicus* (Tin), an engineered variant therefrom or a Taq DNA polymerase variant. In some examples, the DNA polymerase is Bst LF DNA polymerase, GspM LF DNA polymerase, GspSSD LF DNA polymerase, Tin exo-LF DNA polymerase or SD DNA polymerase (see, e.g., WO 2016/189490).

The reverse transcriptase used in the RT-LAMP reaction can be any RT enzyme appropriate for the assay, which can be selected by one of skill in the art. In some embodiments, the RT is from avian myeloblastosis virus (AMV) or Moloney murine leukemia virus (MMLV).

RT-LAMP reactions generally result in the synthesis of large amounts of target nucleic acid, allowing for detection of target nucleic acid from relatively small sample volumes. Furthermore, the large amount of amplification product allows for detection visually or by simple detectors. Although the use of a pH-sensitive indicator dye is exemplified herein, other means for detection of amplification product can be used with the disclosed methods. For example, any one of the following methods can be used to detect RT-LAMP amplification products: (i) fluorescence, using DNA intercalating dyes, fluorescent molecular beacon probes or a fluorescence metal indicator such as calcein; (ii) colorimetry, using a colored indicator for alkaline metal ions, such as hydroxy naphthol blue (Goto et al., *BioTechniques* 46(3): 167-172, 2009) or pH indicators (Tanner et al., *BioTechniques* 58(2):59-68, 2015); (iii) turbidity, as the RT-LAMP reaction produces large amounts of magnesium pyrophosphate (a white precipitate) and dsDNA, which allow visual inspection of results using a turbidimeter (Mori et al., *Biochem Biophys Res Commun*, 289(1):150-154, 2001); (iv) electrochemically, using a pH meter for direct measurement of released hydrogen ions during the RT-LAMP procedure (Xie et al., *Chem Comnum* 50(100): 15932-15935, 2014), or using integrated electrodes for measuring decreases in current resulting from increasing binding of electrochemically-active DNA-binding redox reporters, such as Methylene Blue, to RT-LAMP reaction products (Xie et al., *Biosens Bioelectron* 55:324-329, 2014); (v) enzyme-linked immunosorbent assays (ELISA) or lateral flow immunoassays based on the use of specific probes (Tsai et al., *J Virol Methods* 181(1): 117-124, 2012; Ravan and Yazdanparast, *Anal Biochem* 439(2): 102-108, 2013); (vi) bioluminescence, through bioluminescent output of the coupled conversion of inorganic pyrophosphate produced stoichiometrically during nucleic acid synthesis to ATP by the enzyme ATP sulfurylase (Gandelman et al., *PLoS ONE* 5(11):e14155, 2010).

V. Kits for Detection of ZIKA Nucleic Acid

Also provided herein are kits for detecting ZIKV nucleic acid in a biological sample. The kits include a set of oligonucleotide primers specific for ZIKV nucleic acid. In some embodiments, the set of primers includes (a) six primers each respectively having a sequence at least 90%, at least 95%, at least 96%, at least 97%, at least 98% or at least 99% identical to TGGTTCCACGACATTCCATT (F3 1-1; SEQ ID NO: 1); CATTTCAAGTGGCCAGAGGA (B3 1-1; SEQ ID NO: 2); GGCATGTGCGTCCTTGAACTCTGACACCGGAACTCCACACT (FIP 1-1; SEQ ID NO: 3); AGAAGGAGCAGTTCACACGGCCCCTTGCACCATCCATCTC (BIP 1-1; SEQ ID NO: 4); ACCAGTGCTTCTTTGTTGTTCC (LF 1-1; SEQ ID NO: 5); and CCTGCTGGAGCTCTGGAG (LB 1-1; SEQ ID NO: 6); (b) six primers each respectively having a sequence at least 90%, at least 95%, at least 96%, at least 97%, at least 98% or at least 99% identical to GATCTTGGATGTGGCAGAGG (F3 5-5; SEQ ID NO: 7); TGCTTCTTCCACTTCAGGAC (B3 5-5; SEQ ID NO: 8); CGGGTTCTTCATGACCAGGGCGTTACTACGTCGCCACCATC (FIP 5-5; SEQ ID NO: 9); TCCGTCTTAAGAGTGGGGTCGATGTCACACAGCAACGTGTC (BIP 5-5; SEQ ID NO: 10); CCTTTCAGTFTCTGAACTTGCG (LF 5-5; SEQ ID NO: 11); and CGTCTTCATATGGCGGCTG (LB 5-5; SEQ ID NO: 12); or (c) six primers each respectively having a sequence at least 90%, at least 95%, at least 96%, at least 97%, at least 98% or at least 99% identical to AATGAGTGACCTGGCTAAGC (F3 2-5; SEQ ID NO: 13); AAAAGACACGAGGCCAAGG (B3 2-5; SEQ ID NO: 14); CAGCGCCAGATGAGCTACATCTTTGATGGGTGCCACCTTC (FIP 2-5; SEQ ID NO: 15); AGCGGCATCAAAGTCAGACCATTCACGGGGTGTCCAATT (BIP 2-5; SEQ ID NO: 16); CCTCCAGTGTTCATTTCCGC (LF 2-5; SEQ ID NO: 17); and GCGTFGCTGGTATCTTTCATCTT (LB 2-5; SEQ ID NO: 18).

In some examples, the set of primers includes six primers each respectively having a sequence at least 90%, at least 95%, at least 96%, at least 97%, at least 98% or at least 99% identical to TCGTTCCACGACATTCCATT (F3 1-1; SEQ ID NO: 1); CATTTCAAGTGGCCAGAGGA (B3 1-1; SEQ ID NO: 2); GGCATGTGCGTCCTTGAACTCTGACACCGGAACTCCACACT (FIP 1-1; SEQ ID NO: 3); AGAAGGAGCAGTTCACACGGCCCTTGCACCATC-CATCTC (BIP 1-1; SEQ ID NO: 4); ACCAGTGCTTCTTFTGTTGTTCC (LF 1-1; SEQ ID NO:

5); and CCTTGCTGGAGCTCTGGAG (LB 1-1; SEQ ID NO: 6); and six additional primers each respectively having a sequence at least 90%, at least 95%, at least 96%, at least 97%, at least 98% or at least 99% identical to GATCTG-GATGTGGCAGAGG (F3 5-5; SEQ ID NO: 7); TGCTTCTCCACTCAGGAC (B3 5-5; SEQ ID NO: 8); CGGGTTCTTCATACCAGGGCTTACTACGTCGCCAC-CATC (FIP 5-5; SEQ ID NO: 9); TCCGTCT-TAAGAGTGGGGTGGATGTCACACAGCAACGTGTC (BIP 5-5; SEQ ID NO: 10); CCTTCACTTCTT-GAACTTTGCG (LF 5-5; SEQ ID NO: 11); and CGTCTT-CATATGGCGGCTG (LB 5-5; SEQ ID NO: 12).

In other examples, the set of primers includes six primers each respectively having a sequence at least 90%, at least 95%, at least 96%, at least 97%, at least 98% or at least 99% identical to TGGTTCCACGACATTCCATT (F3 1-1; SEQ ID NO: 1); CATTTCAAGTGGCCAGAGGA (B3 1-1; SEQ ID NO: 2); GGCATGTOCGTCCTT-GAACTCTGACACCGGAACTCCACACT (FIP 1-1; SEQ ID NO: 3); AGAAGGAGCAGTT-CACACGGCCCCTTGCACCATCCATCTC (BIP 1-1; SEQ ID NO: 4): ACCAGTGCTTCTTGTTGTTCC (LF 1-1; SEQ ID NO: 5); and CCTTGCTGGAGCTCTGGAG (LB 1-1; SEQ ID NO: 6); and six additional primers each respectively having a sequence at least 90%, at least 95%, at least 96%, at least 97%, at least 98% or at least 99% identical to AATGAGTGACCTGCCTTAAGC (F3 2-5; SEQ ID NO: 13); AAAAGACACGAGGCCAAGCG (B3 2-5; SEQ ID NO: 14); CAGCGCCAGATGAGCTACATCTTT-GATGGGTGCCACCTTC (FIP 2-5; SEQ ID NO: 15); AGCGGCATTCAAAGTCAGACCATTT-CACGGGGTGTCCAATT (BIP 2-5; SEQ ID NO: 16); CCTCCAGTGTTCATTTCCGC (LF 2-5; SEQ ID NO: 17); and GCGTTGCTGGTATCTTCATCTT (LB 2-5; SEQ ID NO: 18).

In other examples, the set of primers includes six primers each respectively having a sequence at least 90%, at least 95%, at least 96%, at least 97%, at least 98% or at least 99% identical to GATCTTGGATGTGGCAGAGG (F3 5-5; SEQ ID NO: 7); TGCTTCTTCCACTTCAGGAC (B3 5-5; SEQ ID NO: 8); CGGGTTCTTCATGACCAGGGCGTTAC-TACGTCGCCACCATC (FIP 5-5; SEQ ID NO: 9); TCCGTCTTAAGAGTGGGGTOOATOT-CACACAGCAACGTGTC (BIP 5-5; SEQ ID NO: 10); CCTTCACTCTTGAACTTTTGCG (LF 5-5; SEQ ID NO: 1); and CGTCTTCATATGGCGGCTG (LB 5-5; SEQ ID NO: 12); and six additional primers each respectively having a sequence at least 90%, at least 95%, at least 96%, at least 97%, at least 98% or at least 99% identical to AAT-GAGTGACCTGGCTAAGC (F3 2-5; SEQ ID NO: 13); AAAAGACACGAGGCCAAGG (B3 2-5; SEQ ID NO: 14); CAGCGCCAGATGAGCTA-CATCTTTGATGGGTGCCACCTTC (FP 2-5; SEQ ID NO: 15); AGCGGCATT-CAAAGTCAGACCATCACGGGGTGTCCAATC (BIP 2-5; SEQ ID NO: 16); CCTCCAGTGTTCATTTCCGC (LF 2-5; SEQ ID NO: 17); and GCGTTGCTGGTATCTT-CATCTT (LB 2-5; SEQ ID NO: 18).

In yet other examples, the set of primers includes six primers each respectively having a sequence at least 90%, at least 95%, at least 96%, at least 97%, at least 98% or at least 99% identical to TGGTTCCACGACATTCCATT (F3 1-1; SEQ ID NO: 1); CATTTCAAGTGGCCAGAGGA (B3 1-1; SEQ ID NO: 2); GGCATGTGCGTCCTT-GAACTCTGACACCGGAACTCCACACT (FIP 1-1; SEQ ID NO: 3); AGAAGGAGCAGTT-CACACGGCCCCTTGCACCATCCATCTC (BIP 1-1; SEQ ID NO: 4); ACCAGTGCTTCTTTGTGTTCC (LF 1-1; SEQ ID NO: 5); and CCTTGCTGGAGCTCTGGAG (LB 1-1; SEQ ID NO: 6); six additional primers each respectively having a sequence at least 90%, at least 95%, at least 96%, at least 97%, at least 98% or at least 99% identical to GATCTTGGATGTGGCAGAGG (F3 5-5; SEQ ID NO: 7); TGCTTCTCCACTCAGGAC (B3 5-5; SEQ ID NO: 8); CGGGTTCTTCATGACCAGGGCGTTACTACGTCGC-CACCATC (FTP 5-5; SEQ ID NO: 9); TCCGTCT-TAAGAGTGGGGTGGATGTCACACAGCAACGTGTC (BIP 5-5; SEQ ID NO: 10); CCTTTCACTTCTT-GAACTTFGCG (LF 5-5; SEQ ID NO: 11); and CGTCTT-CATATGGCGGCTG (LB 5-5; SEQ ID NO: 12); and six additional primers each respectively having a sequence at least 90%, at least 95%, at least 96%, at least 97%, at least 98% or at least 99% identical to AAT-GAGTGACCTGGCTAAGC (F3 2-5; SEQ ID NO: 13); AAAAGACACGAGGCCAAGG (B3 2-5; SEQ ID NO: 14); CAGCGCCAGATGAGCTACATCTTT-GATGGGTGCCACCTC (FIP 2-5; SEQ ID NO: 15); AGCGGCATTCAAAGTCAGACCATT-CACGGGGTGTCCAAT (BIP 2-5; SEQ ID NO: 16); CCTCCAGTGTTCATTCCGC (LF 2-5; SEQ ID NO: 17); and GCGTTGCTGGTATCTTTCATCTT (LB 2-5; SEQ ID NO: 18).

In specific examples, the set of primers includes (a) six primers each respectively having a sequence comprising or consisting of TGGTTCCACGACATTCCATT (F3 1-1; SEQ ID NO: 1): CATTCAAGTGGCCAGAGGA (B3 1-1; SEQ ID NO: 2); GGCATGTOCGTCCTT-GAACTCTGACACCGGAACTCCACT (FP 1-1; SEQ ID NO: 3); AGAAGGAGCAGTCACACGGCCCCFTGCAC-CATCCATCIC (BIP 1-1; SEQ ID NO: 4): ACCAGTGCTTCTTGTGTTCC (LF 1-1; SEQ ID NO: 5); and CCTTGCTGGAGCTCTGGAG (LB 1-1; SEQ ID NO: 6); (b) six primers each respectively having a sequence comprising or consisting of GATCTTG-GATGTGGCAGAGG (F3 5-5; SEQ ID NO: 7); TGCTCTTCCACTTCAGGAC (B3 5-5; SEQ ID NO: 8); CGGGTTCTCATGACCAGGGCGTTATACGTCGCCAC-CATC (FIP 5-5; SEQ ID NO: 9); TCCGTCT-TAAGAGTGGGGTGGATGTCACACAGCAACGTGTC (BIP 5-5; SEQ ID NO: 10); CCTTTCACTTCTT-GAACTTTGCG (LF 5-5; SEQ ID NO: 11); and CGTCTT-CATATGGCGGCTG (LB 5-5; SEQ ID NO: 12); or (c) six primers each respectively having a sequence comprising or consisting of AATGAGTGACCTGGCTAAGC. (F3 2-5; SEQ ID NO: 13); AAAAGACACGAGGCCAAGG (B3 2-5; SEQ ID NO: 14); CAGCGCCAGATGAGCTA-CATCTTTGATGGGTGCCACCTTC (FIP 2-5; SEQ ID NO: 15); AGCGGCATTCAAAGTCAGACCATT-CACGGGGTGTCCAATT (BIP 2-5; SEQ ID NO: 16); CCTCCAGTGTTCATTTCCGC (LF 2-5; SEQ ID NO: 17); and GCGTTGCTGGTATCTTTCATCTT (LB 2-5; SEQ ID NO: 18).

In other specific examples, the set of primers includes six primers each respectively having a sequence comprising or consisting of TGGTTCCACGACATCCATT (F3 1-1; SEQ ID NO: 1); CATTCAAGTGGCCAGAGGA (B3 1-1; SEQ ID NO: 2); GGCATGTGCGTCCTT-GAACTCTGACACCGGAACTCCACACT (FIP 1-1; SEQ ID NO: 3): AGAAGGAGCAGTT-CACACGGCCCCTTTGCACCATCCATCTC (BIP 1-1; SEQ ID NO: 4); ACCAGTGCTTCTTTGTTCC (LF 1-1; SEQ ID NO: 5); and CCTPGCTGGAGCTCTGGAG (LB 1-1; SEQ ID NO: 6); and six additional primers each respectively having a sequence comprising or consisting of GATCTTGGATGTCAGAGG (F3 5-5; SEQ ID NO: 7);

TGCTTCTTCCACTTCAGGAC (B3 5-5; SEQ ID NO: 8); CGGGTTCTTCATGACCAGGGCGTTACTACGTCGC-CACCATC (FIP 5-5; SEQ ID NO: 9); TCCGTCT-TAAGAGTGGGGTGGATGTCACACAGCAACGTGTC (BIP 5-5; SEQ ID NO: 10); CCTTCACTTCTT-GAACTTTTGCG (LF 5-5; SEQ ID NO: 11); and CGTCTT-CATATGGCGGCTG (LB 5-5; SEQ ID NO: 12).

In other specific examples, the set of primers includes six primers each respectively having a sequence comprising or consisting of TGGTTCCACGACATTCCATT (F3 1-1; SEQ ID NO: 1); CATTTCAAGTGGCCAGAGGA (B3 1-1; SEQ ID NO: 2); GGCATGTGCGTCCTGAACTCTGACACCG-GAACTCCACACT (FIP 1-1; SEQ ID NO: 3); AGAAGGAGCAGTTCACACGGCCCCTTGCACCATC-CATCTC (BIP 1-1; SEQ ID NO: 4); ACCAGTGCTTCTTGTTGTCC (LF 1-1; SEQ ID NO: 5); and CCTTGCTGGAGCTCGGAG (LB 1-1; SEQ ID NO: 6); and six additional primers each respectively having a sequence comprising or consisting of AAT-GAGTGACCTGGCTAAGC (F3 2-5; SEQ ID NO: 13); AAAAGACACGAGGCCAAGG (B3 2-5; SEQ ID NO: 14); CAGCGCCAGATGAGCTACATCTTT-GATGGGTGCCACCTC (FIP 2-5; SEQ ID NO: 15); AGCGGCATTCAAAGTCAGACCATT-CACGGGGTGTCCAAT (BIP 2-5; SEQ ID NO: 16); CCTCCAGTGTTCATTCCGC (LF 2-5; SEQ ID NO: 17); and GCGTTGCTGGTATCTTTCATCTT (LB 2-5; SEQ ID NO: 18).

In other specific examples, the set of primers includes six primers each respectively having a sequence comprising or consisting of GATCTTGGATGTGGCAGAGG (F3 5-5; SEQ ID NO: 7); TGCTTCTTCCACTTCAGGAC (B3 5-5; SEQ ID NO: 8); CGGGTTCTTCATGACCAGGGCGT-TACTACGTCGCCACCATC (FIP 5-5; SEQ ID NO: 9); TCCGTCTTAAGAGTGGGGTGGATGT-CACACAGCAACGTGTC (BIP 5-5; SEQ ID NO: 10); CCTTTCACTTCTTGAACTTTCG (LF 5-5; SEQ ID NO: 11); and CGTCTTCATATGGCGGCTG (LB 5-5; SEQ ID NO: 12); and six additional primers each respectively having a sequence comprising or consisting of AAT-GAGTGACCTGGCTAAGC (F3 2-5; SEQ ID NO: 13); AAAAGACACGAGGCCAAGG (B3 2-5; SEQ ID NO: 14): CAGCGCCAGATGAGCTACATCTTT-GATGGGTGCCACCTTC (FIP 2-5; SEQ ID NO: 15); AGCGGCATTCAAAGTCAGACCATTCACGGGTGTC-CAATT (BIP 2-5; SEQ ID NO: 16); CCTCCAGTGTTCAT-TCCGC (LF 2-5; SEQ ID NO: 17); and GCGTCCTGGTATCTTTCATCTT (LB 2-5; SEQ ID NO: 18).

In one specific non-limiting example, the set of primers includes six primers each respectively having a sequence comprising or consisting of TGGTTCCACGACATCCAT-TCCAT (F3 1-1; SEQ ID NO: 1); CATTT-CAAGTGGCCAGAGGA (B3 1-1; SEQ ID NO: 2); GGCATGTGCGTCCTFGAACTCTGACACCGGAACTC-CACACT (FIP 1-1; SEQ ID NO: 3); AGAAGGAGCAGTT-CACACGGCCCCTTGCACCATCCATCTC (BIP 1-1; SEQ ID NO: 4); ACCAGTGCTCTTGTTGTCC (LF 1-1; SEQ ID NO: 5); and CCTTGCTGGAGCTCTGGAG (LB 1-1; SEQ ID NO: 6); six additional primers each respectively having a sequence comprising or consisting of GATCTTG-GATGTGGCAGAGG (F3 5-5; SEQ ID NO: 7): TGCTCTTCCACTTCAGGAC (B3 5-5; SEQ ID NO: 8); CGGGTTCTTCATGACCAGGGCGTTACTACGTCGC-CACCATC (PIP 5-5; SEQ ID NO: 9); TCCGTCT-TAAGAGTGGGGTGGATGTCACACAGCAACGTGTC (BIP 5-5; SEQ ID NO: 10); CCTTCACTTCTT-GAACTTGCG (LF 5-5; SEQ ID NO: 11); and CGTCTT-CATATOCGCICTG (LB 5-5; SEQ ID NO: 12); and six additional primers each respectively having a sequence comprising or consisting of AAT-GAGTGACCTGGCTAAGC (F3 2-5; SEQ ID NO: 13); AAAAGACACGAGGCCAAGG (B3 2-5; SEQ ID NO: 14): CAGCGCCAGATGAGCTACATCTTTT-GATGGGTGCCACCTTC (FIP 2-5; SEQ ID NO: 15); AGCGGCATTCAAAGTCAGACCATT-CACGGGGTGTCCAATT (BIP 2-5; SEQ ID NO: 16); CCTCCAGTGTTCATTCCGC (LF 2-5; SEQ ID NO: 17); and GCGTTGCTGGTATCTTCATCTT (LB 2-5; SEQ ID NO: 18).

In some embodiments, the kit further includes one or more components for performing an RT-LAMP reaction. In some examples, the kit includes buffer, reverse transcriptase, DNA polymerase, a pH-sensitive indicator dye, dNTPs, master mix, or any combination thereof.

In the disclosed kits, one or more of the oligonucleotide primers (such as one or more of SEQ ID NOs: 1-18), or one or more sets of oligonucleotide primers (such as SEQ ID NOs: 1-6; SEQ ID NOs: 7-12; and/or SEQ ID NOs: 13-18), are provided in one or more containers or in one or more individual wells of a multi-well plate or card. Nucleic acid primers may be provided suspended in an aqueous solution or as a freeze-dried or lyophilized powder, for instance. The container(s) in which the nucleic acid(s) are supplied can be any conventional container that is capable of holding the supplied form, for instance, microfuge tubes, multi-well plates, ampoules, or bottles. The kits can include either labeled or unlabeled nucleic acid primers for use in amplification and/or detection of ZIKV nucleic acids, such as by RT-LAMP.

One or more positive and/or negative control primers and/or nucleic acids also may be supplied in the kit Exemplary negative controls include non-ZIKV nucleic acids (such nucleic acids from other flaviviruses). Exemplary positive controls include purified ZIKV nucleic acid or a vector or plasmid including the ZIKV target sequence. One of skill in the art can select suitable positive and negative controls for the assays disclosed herein.

In some examples, one or more primers (such as one or more sets of primers), are provided in pre-measured single use amounts in individual, typically disposable, tubes, wells, plates, cards, or equivalent containers. In some examples, a set of primers (such as each of SEQ ID NOs: 1-6, each of SEQ ID NOs: 7-12 or each of SEQ ID NOs: 13-18) is included in a single container. In this example, the sample to be tested for the presence of the target nucleic acids can be added to the individual container(s) and amplification and/or detection can be carried out directly. The kit may also include additional reagents for the detection and/or amplification of ZIKV nucleic acids, such as buffer(s), nucleotides (such as dNTPs), enzymes (such as DNA polymerase and/or reverse transcriptase), or other suitable reagents. The additional reagents may be in separate container(s) from the one or more primers or may be included in the same container as the primer(s).

In some examples, the kit includes one or more compounds for detecting an amplification product, such as pH-sensitive indicator dye, a DNA intercalator (e.g., propidium iodide, SYBR green or PICOGREEN fluorescent dyes) a chromogenic or colorimetric reagent (such as hydroxynaphthol blue), or a fluorescent indicator (such as calcein).

VI. Oligonucleotide Primers

Primers (such as isolated nucleic acid primers) suitable for use in the disclosed methods and kits are described herein. In some examples, the primers are suitable for detection of ZIKV nucleic acids by RT-LAMP, such as the assay described herein. RT-LAMP primer sets typically include a forward outer primer (F3), a backward outer primer (B3), a forward inner primer (HP), a backward inner primer (BIP), a forward loop primer (Lop F or LF), and/or a backward loop primer (Loop B or LB). At least some of the RT-LAMP primers are non-naturally occurring nucleic acid molecules, for example, the primers have sequences that do not occur in nature. In particular, the FIP and BIP primers are composed of non-contiguous nucleic acid sequences, and include a portion complementary to a first strand of a double-strand nucleic acid and another portion complement to a second strand of a double-stranded nucleic acid (e.g., reverse complement of a first strand sequence).

In some embodiments, the disclosed primers are between 10 and 60 nucleotides in length (for example 15-50, 20-50, 30-60, or 25-40 nucleotides in length). In some examples, the primers are 10, 11, 12, 13, 14, 15, 16, 17, 18, 19, 20, 21, 22, 23, 24, 25, 26, 27, 28 29, 30, 31, 32, 32, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length and are capable of hybridizing to ZIKV nucleic acid molecules. In some examples, the primers are at least 10, 15, 20, 25, 30, 35, 40, 45, 50, 55, or 60 nucleotides in length. In other examples, the primers may be no more than 20, 25, 30, 35, 40, 45, 50, 55, or 60 nucleotides in length.

In some examples, the disclosed primers include RT-LAMP primers for amplification of ZIKV nucleic acid. The primers include nucleic acid sequences with at least 85% sequence identity (for example, at least 86%, 87%, 88%, 89%, 90%, 91%, 92%, 93%, 94%, 95%, 96%, 97%, 98%, 99%, or 100% identity) to any one of the following:

```
                          (F3 11; SEQ ID NO: 1)
TGGTTCCACGACATTCCATT (B3 1-1; SEQ ID NO: 2)
CATTTCAAGTGGCCAGAGGA (FIP 1-1; SEQ ID NO: 3)
GGCATGTGCGTCCTTGAACTCTGACACCGGAACTCCACACT (BIP 1-1; SEQ ID NO: 4)
AGAAGGAGCAGTTCACACGGCCCCTTTGCACCATCCATCTC (LF 1-1; SEQ ID NO: 5)
ACCAGTGCTTCTTTGTTGTTCC (LB 1-1; SEQ ID NO: 6)
CCTTGCTGGAGCTCTGGAG (F3 5-5; SEQ ID NO: 7)
GATCTTGGATGTGGCAGAGG (B3 5-5; SEQ ID NO: 8)
TGCTTCTTCCACTTCAGGAC (FIP 5-5; SEQ ID NO: 9)
CGGGTTCTTCATGACCAGGGCGTTACTACGTCGCCACCATC (BIP 5-5; SEQ ID NO: 10)
TCCGTCTTAAGAGTGGGGTGGATGTCACACAGCAACGTGTC (LF 5-5; SEQ ID NO; 11)
CCTTTCACTTCTTGAACTTTGCG (LB 5-5; SEQ ID NO: 12)
CGTCTTTCATATGGCGGCTG (F3 2-5; SEQ 1D NO: 13)
AATGAGTGACCTGGCTAAGC (B3 2-5; SEQ ID NO: 14)
AAAAGACACGAGGCCAAGG (FIP 2-5; SEQ ID NO: 15)
CAGCGCCAGATGAGCTACATCTTTTTGATGGGTGCCACCTTC (BIP 2-5; SEQ ID NO: 16)
AGCGGCATTCAAAGTCAGACCATTTCACGGGGTGTCCAATT (LF 2-5; SEQ ID NO: 17)
CCTCCAGTGTTCATTTCCGC (LB 2-5; SEQ ID NO: 18)
GCGTTGCTGGTATCTTTCATCTT
```

In some examples, at least one of the primers includes a detectable label such as a fluorophore, radiolabel, hapten (such as biotin), or chromogen. In some examples, a detectable label is attached (e.g., covalently or non-covalently attached) to an oligonucleotide. The attachment may be to any portion of the oligonucleotide, including to a base, sugar, phosphate backbone, or 5' or 3' end of the oligonucleotide. The label may be directly attached to the oligonucleotide or indirectly attached, for example through a linker molecule. In particular examples, an RT-LAMP primer (e.g., one of SEQ ID NOs: 1-18) includes a fluorophore at the 5' or 3' end. In some examples, the fluorophore is HEX, FAM, TET, fluorescein, fluorescein isothiocyanate (FITC), or QFITC (XRITC). One of skill in the art can select additional suitable fluorophores (see. e.g., *The Molecular Probes Handbook*, Life Technologies, 11th Edition, 2010).

Although exemplary primer sequences are provided herein, the primer sequences can be varied slightly by moving the primer a few nucleotides upstream or downstream from the nucleotide positions that they hybridize to on the target nucleic molecule acid, provided that the probe and/or primer is still specific for the target nucleic acid sequence. For example, variations of the primers disclosed as SEQ ID NOs: 1-18 can be made by "sliding" the probes or primers a few nucleotides 5' or 3' from their positions, and such variations will still be specific for the respective target nucleic acid sequence.

Also provided by the present disclosure are primers that include variations to the nucleotide sequences shown in any of SEQ ID NOs: 1-18, as long as such variations permit detection of the target nucleic acid molecule. For example, a primer can have at least 85%% sequence identity such as at least 86%, 87%, 88%, 89%, 90%, 91%, 92%, 93%, 94%, 95%, 96%, 97%, 98%, or 99% identity to a nucleic acid including the sequence shown in any of SEQ ID NOs: 1-18. In such examples, the number of nucleotides does not change, but the nucleic acid sequence shown in any of SEQ ID NOs: 1-18 can vary at a few nucleotides, such as changes at 1, 2, 3, 4, 5, or 6 nucleotides.

The present application also provides primers that are slightly longer or shorter than the nucleotide sequences shown in any of SEQ ID NOs: 1-18, as long as such deletions or additions permit amplification and/or detection of the desired target nucleic acid molecule. For example, a primer can include a few nucleotide deletions or additions at the 5'- or 3'-end of the primers shown in any of SEQ ID NOs: 1-18, such as addition or deletion of 1, 2, 3, 4, 5, or 6 nucleotides from the 5'- or 3'-end, or combinations thereof (such as a deletion from one end and an addition to the other end). In such examples, the number of nucleotides changes.

Also provided are primers that are degenerate at one or more positions (such as 1, 2, 3, 4, 5, or more positions), for example, a primer that includes a mixture of nucleotides (such as 2, 3, or 4 nucleotides) at a specified position in the primer. In other examples, the primers disclosed herein include one or more synthetic (e.g., non-naturally occurring) bases or alternative bases (such as inosine). In other examples, the primers disclosed herein include one or more modified nucleotides or nucleic acid analogues, such as one or more locked nucleic acids (see, e.g., U.S. Pat. No. 6,794,499), an altered sugar moiety, an inter-sugar linkage, a non-naturally occurring nucleotide linkage, a phosphorothioate oligodeoxynucleotide, a peptide nucleic acid (PNA), or one or more superbases (Nanogen, Inc., Bothell, Wash.).

The nucleic acid primers disclosed herein can be supplied in the form of a kit, for example, for use in the detection or amplification of ZIKV nucleic acid.

The following examples are provided to illustrate certain particular features and/or embodiments. These examples should not be construed to limit the disclosure to the particular features or embodiments described.

EXAMPLES

Example 1: Materials and Methods

This example describes the materials and experimental procedures used for the studies described in Example 2.

Viruses

The following viruses utilized in this study were obtained from the Diagnostic and Reference Laboratory, Arboviral Diseases Branch, DVBD (Fort Collins, Colo.), or the Dengue Branch, DVBD (San Juan. Puerto Rico). ZIKV, strain PRVABC59, was isolated from a human infected in Puerto Rico in 2015. DENV1, strain R99142, was isolated from a traveler who visited Guatemala in 2013. DENV2, strain PR65-98, was isolated from a human in 1998 in Puerto Rico. DENV3, strain 100345, was isolated from a traveler who visited Nicaragua in 2014. DENV4, strain CAREC 08-10822, was isolated from a human specimen from St. Vincent, US Virgin Islands in 2008. CHIKV, strain 103268b, was isolated from a traveler who visited Bolivia in 2015. WNV, strain NY99-35262-11, was isolated from a flamingo at the Bronx zoo, New York, N.Y, in 1999. SLEV, Strain MSI-7, was isolated from a house sparrow in Indianola, Miss., in 1975.

Diagnostic Specimens

A total of 178 acute diagnostic specimens (urine: 84, serum: 94) randomly selected from patients with a ZIKV infection tested at the Centers for Disease Control and Prevention (CDC) by the Trioplex assay for detection of ZIKV, DENV1-4 and CHIKV were included in the study. A total of 68 diagnostic specimens (urine: 27, serum: 41) from patients testing negative for ZIKV infection were also included. Diagnostic specimens were de-identified for this study so that no link could be made between patient identification and assay result.

RT-LAMP Primer Design

ZIKV-specific RT-LAMP primers were designed using the nucleotide sequence of strain PRVABC59 (GenBank accession no. KU501215.1) and PrimerExplorer V5 software. Fifteen different primer sets were designed, and three primer sets (1-1, 2-5 and 5-5) with the most promising initial amplifications were evaluated in the RT-LAMP assay (Table 1). Primer set 1-1 amplifies the region in the ZIKV genome from nucleotides 1626 to 1849 included in the envelope (E) gene. Primer set 2-5 amplifies the region in the ZIKV genome between nucleotides 3682 to 3873 in the non-structural 2a (NS2a) gene. Primer set 5-5 amplifies the region in the ZIKV genome from nucleotides 7901 to 8143 included in the non-structural 5 (NS5) gene.

TABLE 1

Primers and probes used in RT-LAMP and qRT-PCR

| Primer | Sequence | SEQ ID NO: |
|---|---|---|
| F3 1-1 | TGGTTCCACGACATTCCATT | 1 |
| B3 1-1 | CATTTCAAGTGGCCAGAGGA | 2 |
| FIP 1-1 | GGCATGTGCGTCCTTGAACTCTGACACCGGAACTCCACACT | 3 |
| BIP 1-1 | AGAAGGAGCAGTTCACACGGCCCCTTTGCACCATCCATCTC | 4 |
| LF 1-1 | ACCAGTGCTTCTTTGTTGTTCC | 5 |
| LB 1-1 | CCTTGCTGGAGCTCTGGAG | 6 |
| F3 5-5 | GATCTTGGATGTGGCAGAGG | 7 |
| B3 5-5 | TGCTTCTTCCACTTCAGGAC | 8 |
| FIP 5-5 | CGGGTTCTTCATGACCAGGGCGTTACTACGTCGCCACCATC | 9 |
| BIP 5-5 | TCCGTCTTAAGAGTGGGGTGGATGTCACACAGCAACGTGTC | 10 |
| LF 5-5 | CCTTTCACTTCTTGAACTTTGCG | 11 |
| LB 5-5 | CGTCTTTCATATGGCGGCTG | 12 |
| F3 2-5 | AATGAGTGACCTGGCTAAGC | 13 |
| B3 2-5 | AAAAGACACGAGGCCAAGG | 14 |
| FIP 2-5 | CAGCGCCAGATGAGCTACATCTTTTTGATGGGTGCCACCTTC | 15 |
| BIP 2-5 | AGCGGCATTCAAAGTCAGACCATTTCACGGGGTGTCCAATT | 16 |

TABLE 1-continued

Primers and probes used in RT-LAMP and qRT-PCR

| Primer | Sequence | SEQ ID NO: |
|---|---|---|
| LF 2-5 | CCTCCAGTGTTCATTTCCGC | 17 |
| LB 2-5 | GCGTTGCTGGTATCTTTCATCTT | 18 |
| Q1-1F | GGAACTCCACACTGGAACAA | 19 |
| Q1-1R | AACCACGACAGTTTGCCTTT | 20 |
| Q1-1P | [6FAM]AGAGTTCAAGGACGCACATGCCA[BHQ1a-Q] | 21 |

RNA Extraction and In Vitro Transcribed RNA Controls

Viral RNA from samples was extracted from virus supernatant with a QIAmp Viral RNA kit (Qiagen) following the manufacturer's protocols. To prepare in vitro transcribed RNA from the gene region amplified by the 1-1 RT-LAMP primer set for a copy number control, the ZIKV consensus primers (F3 1-1 and B3 1-1) with the T promoter sequence (TAATACGACTCACTATAGGGAGA; SEQ ID NO: 22) added to the 5' end of the F3 1-1 primer were used to amplify a 224 bp segment of cDNA (Table 1). The same size segment of RNA was transcribed from the cDNA using the mMessage mMachine kit (Life Technologies) according to the manufacturer's protocol. RNA was quantified using the RNA Analysis screen tape on the Agilent 4200 Tapestation, and RNA copy numbers/pi were calculated based on spectrophotometry readings.

Viral RNA from 300 d of specimens from spiked serum and urine panels was extracted using the QIAmp Viral RNA kit and eluted in 60 µl of AVE buffer (Qiagen). For diagnostic specimens, viral RNA was extracted from 300 µl of sample using the MagMAX Pathogen RNA/DNA sample preparation system (ThermoFisher Scientific) according to the manufacturer's protocol for low-cell-content samples and eluted in 90 µl of AVE buffer.

Quantitative Reverse-Transcription Polymerase Chain Reaction (qRT-PCR)

ZIKV-specific RNA extracted from samples were analyzed in triplicate by qRT-PCR using the RNA standard described above. A 5 µl aliquot of each purified RNA sample was added to master mix from Quantifast Pathogen RT-PCR kit containing primers and probe designed using the region amplified by the 1-1 RT-LAMP primer set described above. To each reaction, 0.25 µl of 100 µM forward primer Q1-1F, 0.25 µl of 100 µM reverse primer Q1-1R, and 0.15 µl of 25 µM probe Q1-1P were added (Table 1). The reactions were analyzed on a BioRad CFX96 instrument under the following conditions: 50° C. for 20 minutes, 95° C. for 15 minutes, followed by 45 cycles of 95° C. for 15 seconds, and 60° C. for 30 seconds with continuous fluorescence data collection. Average $C_t$ values were calculated based on triplicate wells. If no amplification occurred, a value of 40 was assigned to the well.

RT-LAMP Assay

RT-LAMP reactions were carried out in duplicate in a 25 µl volume containing 1.6 µM each of inner primers FIP and BIP, 0.2 µM each of outer primers F3 and B3, 0.4 µM each of loop primers FL and BL, and either 12.5 µl of 2× Colorimetric LAMP Master Mix (2×; Cat. No. M1800, New England Biolabs) and 10 µl of RNA template, or 5.0 µl of a custom-made 5× Colorimetric LAMP Master Mix and 17.5 µl of RNA template (Tanner et al. BioTechniques 58:59-68, 2015; Poole et al., PLoS One 12(2):e0169011, 2017). Colorimetric LAMP Master Mix (2×) is a low-Tris reaction buffer containing 16.0 mM $MgSO_4$, Bst 2.0 WARMSTART™ DNA Polymerase. WARMSTART™ RTx reverse transcriptase and phenol red for pH detection. LAMP Reactions were incubated at 65° C. between 25 and 40 minutes in a heat block before results were recorded.

Statistical Analysis

Estimates of sensitivity, specificity and (diagnostic) likelihood ratios positive and negative, and accuracy of the ZIKV RT-LAMP assay were calculated based on the results from 110 positive and 68 negative samples by RT-PCR (Pepe, "The statistical evaluation of medical tests for classification and prediction," Oxford; New York: Oxford University Press; 2003, xvi, 302 pages). Wilson's score 95% binomial confidence intervals (CI) were computed for sensitivity and specificity, and score CIs were computed for the likelihood ratios and predictive values (Miettinen et al., Star Med 4(2):213-226, 1985). Estimates of positive and negative predictive values were computed using the estimated likelihood ratios over the full range of pre-test probabilities of ZIKV infection, and these values were displayed graphically. Differences in RT-LAMP positivity by specimen type were evaluated using Fisher's exact test (mid-p).

Estimated Limit of Detection Analysis

At each master mix/primer set combination, the recorded RNA concentrations represent a limit of detection for the individual well measurements, while the algorithm determining positivity of a sample-2 of 3 replicate wells positive-gives a limit of detection (LOD) for the assay as implemented. The expected LOD(s) of the assay are estimated from the reported experiment. The data suggest that the LOD may vary by master mix and primer set, although because the available information limits the ability to model these experimental combinations simultaneously, the LODs are estimated separately.

Since the RNA concentration/dilution sequences differed for two different batches of sample, observations were recorded as one of batch 1 concentrations (1.06, 2.39, 3.74, 4.46, 13.18, 27.10, 345.05 RNA copies/µl) and batch 2 concentrations (0.47, 0.93, 1.67, 3.40, 6.00, 12.00, 116.00 copies/µl) for individual replicate measurements of RNA concentration. This mixing of concentrations and unequal dilution stepping made standard methods for dilution assays not readily applicable. Depending on the master mix/primer set combination, either 6 or 9 replicates were performed. These replicates were grouped in triplicates and the assay algorithm of identifying the second smallest value of the three as the final response for the triplicate set was used (if the smallest two were equal, this value was used), and this yielded either 2 or 3 observations of assay LOD per master mix/primer set combination. The distribution of this final response from the assay algorithm is of interest when making inference regarding the LOD for the assay, since this is the quantity that is used to characterize samples.

The distribution of the assay LOD may be derived from the distribution of the individual replicates by noting that the value of the second-largest observation is the second order statistic of three observations for independent replicates grouped into threes. A model for the distribution of the individual LOD replicates thus readily yields the required distribution for the assay LOD using standard results from the distribution theory of order statistics. Noting that individual replicate responses are reasonably modeled as continuous, positive, skewed right, and interval censored, these values were modeled using standard survival analysis methods assuming either a Weibull (when at least 4 unique values were available) or an exponential (fewer than 4 unique values available); recall the exponential distribution is a special case of the Weibull. Resulting shape and scale estimates therefore provide a model fit for the individual LOD replicates. Denote by $F(x; r,\lambda)$ the cumulative distribution function (CDF) of the Weibull distribution with shape parameter r and scale parameter $\lambda$; r is fixed at 1 for the exponential distribution. The resulting CDF of the distribution of the assay LOD is, therefore, $F_{2;3}(x;r,\lambda)=F(x;r,\lambda)=F(x; r,\lambda)^2[3-2F(x; r,\lambda)]$, where the subscript 2;3 indicates the second order statistic of a sample of size three.

Implementing the survival analysis approach described provides maximum likelihood estimates $\hat{r}$ and $\hat{\lambda}$ in the case of the Weibull, and $\hat{\lambda}$ for the exponential, and these may be used directly in the expression for $F_{x,y}(x;r, \lambda)$, giving an estimate of the distribution for the assay LOD. The expected assay LOD is thus the mean of this distribution, which must be computed numerically using the probability density function derived from $F_{2;3}(x; r, \lambda)$ and numerical integration. Confidence intervals for the mean assay LOD may theoretically be computed using asymptotic results, but with few observations here, instead bootstrap resampling was used (Davidson and Hinkley, "Bootstrap methods and their application," Cambridge; New York, N.Y., USA: Cambridge University Press; 1997). Briefly, the 6 or 9 individual replicates were resampled with replacement 10,000 times, and for each of these resample datasets, maximum likelihood estimates $\hat{r}$ and $\hat{\lambda}$ were computed and the mean of $F_{2;3}(x;\hat{r},\hat{\lambda})$ calculated. The average of these 10,000 bootstrap resample values of the mean assay LOD are the final estimates for the assay LOD, while the empirical 2.5th and 97.5th quantile points of the 10,000 bootstrap resample values provide a 95% confidence interval (CI) for the mean assay LOD. Estimates of the mean assay LOD (95% CI) are reported in Table 2.

Example 2: RT-LAMP Assay for Detection of ZIKV RNA

This example describes optimization and characterization of an RT-LAMP assay to detect ZIKV in urine and serum samples. The studies described in this example report results obtained from primer sets 1-1, 2-5 and 5-5.

Optimization and Amplification Efficiency of ZIKV RT-LAMP Assay

Viral RNA extracted from ZIKV-infected Vero cell supernatant was used as a template to determine optimal reaction conditions for the RT-LAMP assay. RNA copies/µl were quantitated using qRT-PCR and determined to be $4.8 \times 10^6$ RNA copies/µl. Varying dilutions of viral RNA from 100 to 0.625 RNA copy/µl were made and tested in the RT-LAMP assay using primer sets 1-1, 2-5, 5-5 and combinations of primer sets (1-½-5, 1-⅕-5, 2-5/5-5, and 1-½-5/5-5) at 65° C. Reaction results were recorded between 20 to 40 minutes in 5 minute intervals. Detection of nucleic acid amplification was determined visually with a color change from pink to yellow indicating amplification of nucleic acid. The reaction was considered complete once the non-template control (NTC) wells began to change color. The duration of this color change occurred between 30 and 40 minutes and was dependent on each individual primer set Results were recorded at the 5-minute time interval in which all NTC wells were still negative for the primer set evaluated. Reactions were considered positive when 2 of the 3 wells displayed a color change. Two or three independent tests conducted in triplicate were used to calculate the expected limits of detection for each primer set. Primer sets were tested with both the 2×LAMP master mix (MM) commercially available (New England Biolabs) and a 5XMM which allowed for an additional 7.5 µl of RNA to be added to the reaction.

A decrease in the limit of detection was observed for all primer sets in the reaction using 5XMM and subsequent higher volumes of viral RNA with one exception (primer set 5-5). Primer sets 1-1 and 1-½-5/5-5 had the greatest decrease in the expected limit of detection from 19.3 and 8.5 RNA copies/µl, respectively, using the 2XMM and 10 µl of RNA in the reaction to 7.2 and 2.1 RNA copies/d, respectively, in the reaction containing 5XMM concentration and 17.5 µl of RNA. Primer set 1-⅕-5 also had a notable decrease in the expected limit of detection from 10.0 RNA copies/µl with 2XMM to 5.4 RNA copies/µl with 5XMM. Relatively similar values were recorded for primer set 5-5 (6.2 RNA copies/µl and 6.6 RNA copies/µl with 2XMM and 5XMM, respectively) and primer set 2-5 (3.9 and 3.4 RNA copies/µl with 2XMM and 5XMM, respectively). Using the 5XMM, primer sets 1-½-5 and 1-½-5/5-5 were found to have the lowest expected limit of detection in the assay at 2.1 RNA copies/µl (Table 2). Three primer sets (2-5, 1-½-5 and 1-½-5/5-5) were subsequently tested for their ability to detect viral RNA in a panel of virus-spiked human serum specimens.

TABLE 2

Estimates (95% CI) of mean ZIKV RT-LAMP assay limit of detection for each primer set using 2X and 5X master mix (MM)

| Primer set | 2XMM | 5XMM |
| --- | --- | --- |
| 1-1 | 19.3[a] (9.5, 38.8)[b] | 7.2 (3.9, 11.8) |
| 2-5 | 3.9 (2.9, 5.0) | 3.4 (2.5, 4.2) |
| 5-5 | 6.2 (3.7, 9.7) | 6.6 (3.6, 10.8) |
| 1-1/2-5 | 4.7 (3.5, 5.8) | 2.1 (1.4, 2.7) |
| 1-1/5-5 | 10.0 (6.6, 13.1) | 5.4 (3.4, 9.5) |
| 2-5/5-5 | 4.3 (3.0, 5.5) | 2.8 (2.3, 3.2) |
| 1-1/2-5/5-5 | 8.5 (4.6, 15.4) | 2.1 (1.4, 2.9) |

[a] RNA copies/µl. The mean of the expected limit of detection was determined using ZIKV viral RNA with quantitated RNA copies measured by qRT-PCR using the gene region amplified by primer set 1-1. Reactions were incubated at 65° C. for 20-40 minutes before results were recorded.
[b] 95% confidence interval Sensitivity of ZIKV RT-LAMP assay To evaluate the sensitivity of the ZIKV RT-LAMP assay compared to qRT-PCR, viral RNA was extracted from 300 µl of sample from a virus-spiked serum panel and tested with primer sets 2-5, 1-½-5 and 1-½-5/5-5. The RNA in each sample was quantitated by qRT-PCR and ranged from 2.8 to 1476 RNA copies/pi. Ct values were also recorded. A positive result in the qRT-PCR is any average Ct value under 38.0 from triplicate wells while a negative test result is any average Ct value over 38.0 from triplicate wells. A Ct value of 40.0 was assigned if no amplification occurred in one of the triplicate wells. Ct values in the serum panel for samples containing ZIKV RNA ranged from 27.6 to 36.3 (Table 3). All primer sets reacted similarly when tested with the virus-spiked serum samples. All primer sets were able to detect viral RNA in samples containing more than 50 RNA copies/µl. Only 1-½-5/5-5 was not able to detect viral RNA in the sample (#9) containing 12.5 RNA copies/µl. None of the primer sets were able to detect viral RNA in sample (#1) containing 2.8 RNA copies/µl. This is not surprising since the limit of detection of the assay was determine to be in the range of 2.7 and 3.9 RNA copies/l using diluted viral RNA. No false positive results were detected for any of the negative samples included in the panel with any primer set (Table 3).

TABLE 3

Sensitivity of RT-LAMP with ZIKV serum panel

| Sample | RNA copies/µl[a] | Ct value[b] | RT-LAMP[c] 2-5 | 1-½-5 | 1-½-5/5-5 |
|---|---|---|---|---|---|
| 1 | 2.8 | 36.3 | − | − | − |
| 2 | 0 | >40.0 | − | − | − |
| 3 | 164 | 30.6 | + | + | + |
| 4 | 0 | >40.0 | − | − | − |
| 5 | 104 | 31.3 | + | + | + |
| 6 | 55 | 32.1 | + | + | + |
| 7 | 1476 | 27.6 | + | + | + |
| 8 | 0 | >40.0 | − | − | − |
| 9 | 12.5 | 34.2 | + | + | − |
| 10 | 544 | 29.0 | + | + | + |
| 11 | 368 | 29.5 | + | + | + |
| 12 | 0 | 38.9 | − | − | − |

[a]RNA copies/µl in each sample were evaluated in qRT-PCR using in vitro transcribed RNA encompassing the gene region amplified by primer set 1-1.
[b]Average Ct values of the quantitated serum panel based on primers from gene region amplified by primer set 1-1 (5 µl RNA/reaction).
[c]sensitivity of RT-LAMP was evaluated with each primer set using 5X MM. Reactions were incubated at 65° C. for 20-40 minutes before results were recorded as positive (+) or negative (−).

The assay was also evaluated using a panel of urine samples spiked with varying concentrations of ZIKV RNA. ZIKV RNA concentrations in the panel ranged from 1.2 to 7047 RNA copies/l and Ct values ranged from 23.1 to 35.5 for samples containing ZIKV RNA (Table 4). Similar results to the serum panel were obtained for the urine panel. When the assay was performed using primer sets 2-5 and 1-½-5, all samples containing ZIKV RNA except the samples with the least amount of RNA (sample #4, 1.2 RNA copies/µl and sample #2, 12 RNA copies/µl) were detected (Table 4). No false positive results were detected for any of the negative samples included in the panel with either primer set (Table 4).

TABLE 4

Sensitivity of RT-LAMP with ZIKV urine panel

| Sample | RNA copies/µl[a] | Ct value[b] | RT-LAMP[c] 2-5 | 1-½-5 |
|---|---|---|---|---|
| 1 | 316 | 27.5 | + | + |
| 2 | 12 | 33.7 | − | − |
| 3 | 44 | 30.3 | + | + |
| 4 | 1.2 | 35.5 | − | − |
| 5 | 0 | 41.4 | − | − |
| 6 | 0 | 39.9 | − | − |
| 7 | 7047 | 23.1 | + | + |
| 8 | 0 | 39.1 | − | − |

[a]RNA copies/µl in each sample were evaluated in qRT-PCR using RNA transcript made within the gene region amplified by primer set 1-1.
[b]Average Ct values of the quantitated urine panel based on primers from gene region amplified by primer set 1-1 (5 µl RNA/reaction).
[c]Sensitivity of RT-LAMP was evaluated with each primer set using 5X MM. Reactions were incubated at 65° C. for 20-40 minutes before results were recorded as positive (+) or negative (−).

A panel consisting of a variety of diagnostic specimens including whole blood, serum, and urine with and without nucleic acid preservative was also evaluated in the RT-LAMP assay with primer set 1-½-5 to determine the sensitivity and specificity of the assay compared to qRT-PCR results. The sensitivity of the qRT-PCR described here was validated in a separate experiment with quantitated viral RNA and displayed an equivalent sensitivity compared to the CDC's single-plex real-time RT-PCR assay. RNA was extracted from 300 µl of sample and eluted in 100 µl AVE buffer. Results from the CDC's single-plex real-time RT-PCR assay for the detection of ZIKV using 20 µl of RNA and the ZIKV RT-LAMP assay using 17.5 µl of RNA were compared. RNA concentrations using the qRT-PCR along with the Ct values for this PCR were included in the analysis for each sample (Table 5). The ZIKV RT-LAMP assay was comparable to the CDC's single-plex qRT-PCR when tested with the specimen panel with only two false negative samples recorded (#2, 3.3 RNA copies/µl and #8 9.6 RNA copies/µl). The same RNA used in the single-plex real-time RT-PCR was used for the LAMP assay and the PCR for quantitation, but had been freeze-thawed between uses possibly resulting in degradation of the RNA sample which may account for the drop in Ct values between the two PCR tests for all samples and the negative reactions in the ZIKV RT-LAMP for samples #2 and #8. Overall, when compared to the single-plex real-time RT-PCR the RT-LAMP assay had a sensitivity of 80% (95% CI 49.0±94.3%) and specificity of 100% (95% CI 75.7±100%). While the sample size was low, these results provide confidence that the ZIKV RT-LAMP assay should perform well with a large set of diagnostic specimens when compared to the qRT-PCR assay.

TABLE 5

Performance of RT-LAMP with a proficiency panel of diagnostic specimens

| Sample | Ct value[a] | Ct value 1-1[b] | RNA copies/µl[c] | RT-LAMP[d] |
|---|---|---|---|---|
| 1 | >40.0 | >40.0 | 0 | − |
| 2 | 36.4 | 37.4 | 3.3 | − |
| 3 | >40.0 | >40.0 | 0 | − |
| 4 | 29.7 | 33.3 | 47.8 | + |
| 5 | 38.0 | >40.0 | 0 | − |
| 6 | 30.5 | 32.7 | 71.2 | + |
| 7 | >40.0 | >40.0 | 0 | − |
| 8 | 32.5 | 35.4 | 9.6 | − |
| 9 | 31.3 | 36.7 | 11.1 | + |
| 10 | 32.3 | 34.5 | 18.5 | + |
| 11 | >40.0 | >40.0 | 0 | − |
| 12 | 32.4 | 36.5 | 5.2 | + |
| 13 | 38.1 | >40.0 | 0 | − |
| 14 | >40.0 | >40.0 | 0 | − |
| 15 | >40.0 | >40.0 | 0 | − |
| 16 | 30.5 | 33.7 | 35.1 | + |

TABLE 5-continued

Performance of RT-LAMP with a proficiency panel of diagnostic specimens

| Sample | Ct value[a] | Ct value 1-1[b] | RNA copies/μl[c] | RT-LAMP[d] |
|---|---|---|---|---|
| 17 | >40.0 | >40.0 | 0 | − |
| 18 | 31.9 | 35.3 | 10.3 | + |
| 19 | 38.3 | >40.0 | 0 | − |
| 20 | 28.9 | 32.0 | 124.6 | + |
| 21 | >40.0 | >40.0 | 0 | − |
| 22 | >40.0 | >40.0 | 0 | − |

[a]Average Ct values based on the CDC RT-PCR single-plex assay using freshly extracted RNA run in duplicate wells for the detection of ZIKV.
[b]Average Ct values of the qRT-PCR after freeze-thawing of RNA based on primers from gene region amplified by primer set 1-1 (5 μl RNA/extraction).
[c]RNA copies/μl in each sample were evaluated in qRT-PCR after freeze-thawing of RNA using RNA transcript made within the gene region amplified by primer set 1-1.
[d]Sensitivity of RT-LAMP was evaluated with primer set 1-1/2-5 and 5X MM. Reactions were incubated at 65° C. for 20-40 minutes before results were recorded as positive (+) or negative (−).

positive was 2.5 (95% CI 0.8-7.4), and the likelihood ratio negative was 0.9 (95% CI 0.8-1.0). When diagnostic specimens had RNA concentrations >1.0 copy/μl (Ct values ranging 35.20 to 24.23) the ZIKV RT-LAMP assay was able to detect 54 out of 67 positive samples, a sensitivity of 80.6% (95% CI 69.6-89.3%); there were no RT-PCR negative samples, so specificity and the likelihood ratios could not be estimated. These results are summarized in FIG. 1 which separates negative and positive RT-LAMP results and plots them based on the Ct value from the real-time RT-PCR and RNA concentration. When all diagnostic samples were included in the statistical analysis, the assay had a sensitivity of 54.5% (95% CI 45.2-63.5%), specificity of 94.1% (95% CI 85.8-97.7%), likelihood ratio positive of 9.3 (95% CI 3.8-23.9) and likelihood ratio negative of 0.5 (95% CI 0.4-0.6). The overall accuracy of the ZIKV RT-LAMP assay was 69.7% (95% CI 62.6-75.9%) (Table 6).

TABLE 6

Diagnostic performance of RT-LAMP based on RNA concentration

| RNA copies/μl | Sensitivity (%) | Specificity (%) | Likelihood Ratio Positive | Likelihood Ratio Negative | Accuracy (%) |
|---|---|---|---|---|---|
| <1.0 | 14.0 (5.4-28.5)* | 94.1 (85.8-97.7) | 2.5 (0.8-7.4) | 0.9 (0.8-1.0) | 63.1 (53.8-71.5) |
| >1.0 | 80.6 (69.6-89.3) | N/A** | N/A** | N/A** | 80.6 (69.6-88.3) |
| total | 55.4 (45.2-63.5) | 94.1 (85.8-97.7) | 9.3 (3.8-23.9) | 0.5 (0.4-0.6) | 69.7 (62.6-75.9) |

*95% confidence interval;
**no samples were RT-PCR negative

Specificity of ZIKV RT-LAMP Assay

In order to estimate the specificity of the assay to detect only ZIKV RNA, a panel of urine samples spiked with varying concentrations of arboviruses including DENV1 (1.1 $\log_{10}$ PFU/μl), DENV2 (4.9 $\log_{10}$ PFU/μl), DENV3 (0.2 $\log_{10}$ PFU/μl). DENV4 (0.3 $\log_{10}$ PFU/μl). WNV (3.6 $\log_{10}$ PFU/μl) SLEV (4.1 $\log_{10}$ PFU/μl), and CHIKV (0.1 PFU/μl) were tested. RNA was extracted from 300 μl of spiked urine and tested in the assay using primer set 1-½-5 under the same conditions as previously described. The ZIKV RT-LAMP assay was shown to be highly specific for ZIKV since none of the spiked urine samples with other arboviruses were positive in the assay. Additionally, A panel of diagnostic specimens which tested positive in the CDC's diagnostic Trio-plex RT-PCR assay for DEN V (n=10) with Ct values ranging from 15.77 to 31.92 or CHIKV (n=10) with Ct values ranging from 18.47 to 24.23, were negative when tested in the ZIKV RT-LAMP assay.

Evaluation of RT-LAMP Assay for Clinical Diagnosis of ZIKV

Figure 2:
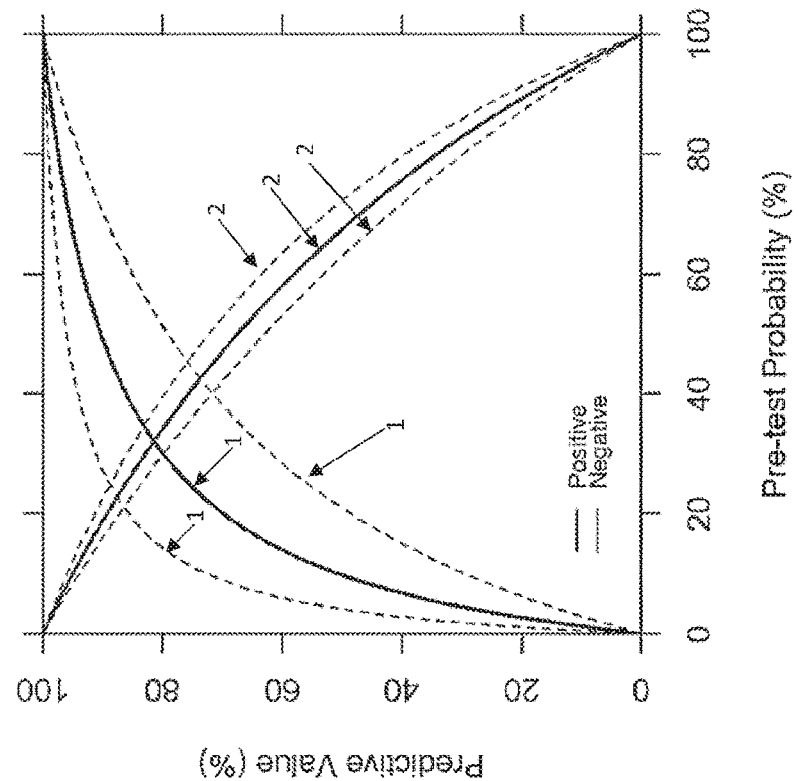
FIG. 2: Predictive values for the ZIKV RT-LAMP assay based on pre-test probability percentages of ZIKV infection. Positive (1—solid line) and negative (2—solid line) predictive values (%), and 95% confidence intervals (positive: 1—dashed lines, negative: 2—dashed lines), plotted against pre-test probability (%) for the RT-LAMP assay using all diagnostic samples combined.

A total of 178 diagnostic specimens (94 serum specimens and 84 urine specimens) were collected for testing in the ZIKV RT-LAMP assay. Of these, 110 were positive for ZIKV by qRT-PCR (53 ZIKV-positive serum samples, 57 ZIKV-positive urine samples), and 68 were negative by qRT-PCR (41 ZIKV negative serum samples, 27 ZIKV negative urine samples). When diagnostic specimens had RNA concentrations <1.0 copy/μl (Ct values ranging from 35.09 to 40.00), the ZIKV RT-LAMP assay was only able to detect 6 of 43 positive samples, a sensitivity rate of only 14.0% (95% CI 6.6-27.3%), while 64 of 68 RT-PCR negative samples were RT-LAMP negative, for a specificity of 94.1% (95% CI 85.8-97.7%) (FIG. 1). The likelihood ratio FIG. 2 shows the predictive values (and 95% CIs) for the ZIKV RT-LAMP assay based on pre-test probability percentages of ZIKV infection. When the pre-test probability of ZIKV infection in the population was plotted against the positive and negative predictive values of the ZIKV RT-LAMP assay, the test is estimated to maximize both predictive values simultaneous when the pre-test probability of disease is approximately 30% (FIG. 2). No statistical difference in RT-LAMP positivity by specimen type were detected in either PCR positive (Fisher's exact mid-p=0.9) or PCR negative (Fisher's exact mid-p=0.7) samples.

Diagnostic Applications

Described herein is the development of RT-LAMP for the rapid detection of ZIKV in urine and serum. The ZIKV RT-LAMP assay demonstrated a level of detection similar to RT-PCR when the Ct value was below 35.2 corresponding to an RNA concentration of 21.0 RNA copies/μl, resulting in an accuracy rate of 80.6%. When the analysis included samples with an RNA concentration of <1.0 RNA copies/μl, the accuracy of the diagnostic test dropped to 69.7%. The ZIKV RT-LAMP assay also demonstrated a high degree of specificity with only a 2.2% false positive rate calculated from negative diagnostic specimens tested in the assay; the false negative rate was 27.5%.

These results indicate that the ZIKV RT-LAMP assay can be used as a rapid point-of-care test for clinical screening of suspected ZIKV infections or routine testing for ZIKV infections in asymptomatic pregnant women. RT-LAMP offers an easy to use, convenient and cost-effective alternative to laboratory-based testing, particularly in field or clinical settings where the rapidity and convenience of screening diagnostic samples may outweigh the need for definitive diagnoses. In this study, the median value of RNA concentration from specimens detected by qRT-PCR was 1.92 RNA copies/μl (a median Ct value of 34.09). These specimens and values for qRT-PCR are typical of diagnostic specimens tested for ZIKV, and it is believed this study accurately demonstrates the level of sensitivity that can be obtained with RT-LAMP.

Using the rapid point-of-care RT-LAMP assay disclosed herein can greatly enhance prenatal care of women living in areas where ZIKV may circulate. By utilizing this diagnostic screening tool for the detection of ZIKV infections in asymptomatic pregnant women throughout pregnancy more information will be available to health care providers and patients during critical times of care.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method for detecting Zika virus (ZIKV) RNA in a biological sample, comprising:
   (i) subjecting the sample to a reverse transcription loop-mediated isothermal amplification (RT-LAMP) reaction using a set of primers specific for ZIKV nucleic acid to produce a ZIKV nucleic acid amplification product, wherein the set of primers comprises six primers each respectively having a sequence at least 90% identical to SEQ ID NO: 13, SEQ ID NO: 14, SEQ ID NO: 15, SEQ ID NO: 16, SEQ ID NO: 17 and SEQ ID NO: 18; and
   (ii) detecting the ZIKV nucleic acid amplification product, thereby detecting ZIKV RNA in the biological sample.

2. The method of claim 1, wherein the set of primers comprises:
   (a) six primers each respectively having a sequence consisting of SEQ ID NO: 13, SEQ ID NO: 14, SEQ ID NO: 15, SEQ ID NO: 16, SEQ ID NO: 17 and SEQ ID NO: 18;
   (b) six primers each respectively having a sequence consisting of SEQ ID NO: 1, SEQ ID NO: 2, SEQ ID NO: 3, SEQ ID NO: 4, SEQ ID NO: 5 and SEQ ID NO: 6; and
   (c) six primers each respectively having a sequence consisting of SEQ ID NO: 7, SEQ ID NO: 8, SEQ ID NO: 9, SEQ ID NO: 10, SEQ ID NO: 11 and SEQ ID NO: 12.

3. The method of claim 1, wherein the set of primers further comprises:
   six primers each respectively having a sequence at east 90% identical to SEQ ID NO: 1, SEQ ID NO: 2, SEQ ID NO: 3, SEQ ID NO: 4, SEQ ID NO: 5 and SEQ ID NO: 6; and/or
   six primers each respectively having a sequence at east 90% identical to SEQ ID NO: 7, SEQ ID NO: 8, SEQ ID NO: 9, SEQ ID NO: 10, SEQ ID NO: 11 and SEQ ID NO: 12.

4. The method of claim 1, wherein the RT-LAMP reaction is performed at about 65° C.

5. The method of claim 1, wherein the RT-LAMP reaction includes a pH-sensitive indicator dye.

6. The method of claim 5, wherein the pH-sensitive indicator dye is a colored dye detectable in visible light.

7. The method of claim 6, wherein the pH-sensitive indicator dye comprises cresol red, phenol red, m-cresol purple, bromocresol purple, neutral red, naphtholphthalein, thymol blue or naptolphthalein.

8. The method of claim 5, wherein the pH-sensitive indicator dye is a fluorescent indicator dye.

9. The method of claim 8, wherein the fluorescent dye comprises 2',7'-bis-(2-carboxyethyl)-5(6)-carboxyfluorescein, 5(6)-carboxy-2', 7'-dichlorofluorescein, 5(6)-carboxyfluorescein, 3,6-diacetoxyphthalonitrile, 6,8-dihydroxy-1,3-pyrenedisulfonic acid, or 5-(and-6)-carboxyl seminaphthorhodafluor.

10. The method of claim 1, wherein detecting the ZIKV nucleic acid amplification product comprises detecting a visible color change.

11. The method of claim 1, wherein detecting the ZIKV nucleic acid amplification product comprises detecting fluorescence.

12. The method of claim 1, wherein the biological sample is a biological fluid sample.

13. The method of claim 12, wherein the biological fluid sample comprises a urine or serum sample.

14. A kit for detecting Zika virus (ZIKV) RNA in a biological sample, comprising a set of oligonucleotide primers, wherein the set of primers comprises six primers each respectively having a sequence at least 90% identical to SEQ ID NO: 13, SEQ ID NO: 14, SEQ ID NO: 15, SEQ ID NO: 16, SEQ ID NO: 17 and SEQ ID NO: 18.

15. The kit of claim 14, further comprising:
six primers each respectively having a sequence at least 90% identical to SEQ ID NO: 1, SEQ ID NO: 2, SEQ ID NO: 3, SEQ ID NO: 4, SEQ ID NO: 5 and SEQ ID NO: 6; or
six primers each respectively having a sequence at least 90% identical to SEQ ID NO: 7, SEQ ID NO: 8, SEQ ID NO: 9, SEQ ID NO: 10, SEQ ID NO: 11 and SEQ ID NO: 12.

16. The kit of claim 14, further comprising:
six primers each respectively having a sequence at least 90% identical to SEQ ID NO: 1, SEQ ID NO: 2, SEQ ID NO: 3, SEQ ID NO: 4, SEQ ID NO: 5 and SEQ ID NO: 6; and
six primers each respectively having a sequence at least 90% identical to SEQ ID NO: 7, SEQ ID NO: 8, SEQ ID NO: 9, SEQ ID NO: 10, SEQ ID NO: 11 and SEQ ID NO: 12.

17. The kit of claim 14, wherein the set of primers comprises six primers each respectively having a sequence consisting of SEQ ID NO: 13, SEQ ID NO: 14, SEQ ID NO: 15, SEQ ID NO: 16, SEQ ID NO: 17 and SEQ ID NO: 18.

18. The kit of claim 17, wherein the set of primers further comprises:
six primers each respectively having a sequence consisting of SEQ ID NO: 1, SEQ ID NO: 2, SEQ ID NO: 3, SEQ ID NO: 4, SEQ ID NO: 5 and SEQ ID NO: 6; or
six primers each respectively having a sequence consisting of SEQ ID NO: 7, SEQ ID NO: 8, SEQ ID NO: 9, SEQ ID NO: 10, SEQ ID NO: 11 and SEQ ID NO: 12.

19. The kit of claim 17, wherein the set of primers further comprises:
six primers each respectively having a sequence consisting of SEQ ID NO: 1, SEQ ID NO: 2, SEQ ID NO: 3, SEQ ID NO: 4, SEQ ID NO: 5 and SEQ ID NO: 6; and
six primers each respectively having a sequence consisting of SEQ ID NO: 7, SEQ ID NO: 8, SEQ ID NO: 9, SEQ ID NO: 10, SEQ ID NO: 11 and SEQ ID NO: 12.

20. The kit of claim 14, further comprising buffer, reverse transcriptase, DNA polymerase, or any combination thereof.

* * * * *

UNITED STATES PATENT AND TRADEMARK OFFICE
CERTIFICATE OF CORRECTION

| | |
|---|---|
| PATENT NO. | : 11,708,613 B2 |
| APPLICATION NO. | : 16/609994 |
| DATED | : July 25, 2023 |
| INVENTOR(S) | : Amanda E. Calvert |

It is certified that error appears in the above-identified patent and that said Letters Patent is hereby corrected as shown below:

In the Claims

Claim 3, Column 38, Line 40, "at east" should read –at least–

Claim 3, Column 38, Line 44, "at east" should read –at least–

Signed and Sealed this
Nineteenth Day of September, 2023

*Katherine Kelly Vidal*
Katherine Kelly Vidal
*Director of the United States Patent and Trademark Office*